US011839585B2

(12) United States Patent
Johnson et al.

(10) Patent No.: US 11,839,585 B2
(45) Date of Patent: Dec. 12, 2023

(54) RESUSCITATION AND VENTILATION ASYNCHRONY MONITOR

(71) Applicant: The Regents of the University of California, Oakland, CA (US)

(72) Inventors: Michael Austin Johnson, Sacramento, CA (US); Jason Adams, Sacramento, CA (US); Jean-Pierre Delplanque, Davis, CA (US); Justin Koos, Sacramento, CA (US); Gregory Rehm, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 17/898,182

(22) Filed: Aug. 29, 2022

(65) Prior Publication Data

US 2023/0138861 A1    May 4, 2023

Related U.S. Application Data

(63) Continuation of application No. 16/348,795, filed as application No. PCT/US2017/061162 on Nov. 10, 2017, now Pat. No. 11,464,703.
(Continued)

(51) Int. Cl.
*A61B 5/00*   (2006.01)
*A61H 31/00*  (2006.01)

(52) U.S. Cl.
CPC .......... *A61H 31/00* (2013.01); *A61B 5/0022* (2013.01); *A61B 5/7203* (2013.01);
(Continued)

(58) Field of Classification Search
CPC ..................................................... A61B 5/742
See application file for complete search history.

(56) References Cited

U.S. PATENT DOCUMENTS 6,848,444 B2    2/2005   Smith et al.
8,638,200 B2 *  1/2014   Milne ............... A61B 5/0871
                                          340/286.07
(Continued)

FOREIGN PATENT DOCUMENTS

CN    101500633 A    8/2009
CN    102512736 A    6/2012
(Continued)

OTHER PUBLICATIONS

Extended European Search Report dated Mar. 27, 2020, from application No. 17869396.6.
(Continued)

*Primary Examiner* — Travis R Hunnings
(74) *Attorney, Agent, or Firm* — MARSHALL, GERSTEIN & BORUN LLP

(57) ABSTRACT

Resuscitation and ventilation monitoring devices are provided. A device includes an inlet in fluid communication with airflows exchanged with lungs of a patient and an airflow meter for measuring characteristics of the airflows. A user may provide a controller with patient information, e.g., height, weight, gender, or age, via a measurement selector, enabling the controller to determine acceptable ranges of measured airflow characteristics. The device may determine a current mode of ventilation and associated ventilator settings based on the measured airflow characteristics. The device may also identify and filter out artifacts present in the ventilation signal, and determine whether a respiratory failure phenotype is present in the ventilation. If the current mode of ventilation and associated ventilator settings fall outside an acceptable range, the ventilation is
(Continued)

classified as off-target and the controller may cause a sensory alarm to alert the user. The device may suggest a corrective action based on the type of off-target ventilation detected. The device may also continuously analyze ventilation to determine changes in lung compliance over time and to identify pathological changes over time. The device may work within a network of devices and user interfaces via wired or wireless communication, and is not restricted to or dependent on the type of ventilatory device with which a patient is being supported.

35 Claims, 13 Drawing Sheets

Related U.S. Application Data

(60) Provisional application No. 62/420,943, filed on Nov. 11, 2016.

(52) U.S. Cl.
CPC .......... *A61B 5/7264* (2013.01); *A61B 5/7282* (2013.01); *A61B 5/742* (2013.01); *A61B 5/7405* (2013.01); *A61H 2201/5023* (2013.01); *A61H 2201/5087* (2013.01)

(56) References Cited

U.S. PATENT DOCUMENTS

| 11,464,703 | B2 | 10/2022 | Johnson et al. |
|---|---|---|---|
| 2005/0119586 | A1 | 6/2005 | Coyle et al. |
| 2006/0069326 | A1 | 3/2006 | Heath |
| 2007/0000494 | A1 | 1/2007 | Banner et al. |
| 2008/0236582 | A1 | 10/2008 | Tehrani |
| 2008/0236585 | A1 | 10/2008 | Parker et al. |
| 2012/0133519 | A1 | 5/2012 | Milne et al. |
| 2012/0291784 | A1* | 11/2012 | Robinson .......... A61M 16/0057 128/204.23 |
| 2013/0317753 | A1* | 11/2013 | Kamen .................. H04L 45/02 600/595 |
| 2014/0088374 | A1 | 3/2014 | Sullivan et al. |
| 2014/0296728 | A1* | 10/2014 | Sinderby ................ A61B 5/392 600/529 |
| 2017/0325695 | A1* | 11/2017 | Freeman ................ A61B 5/053 |
| 2019/0336085 | A1 | 11/2019 | Kayser et al. |
| 2021/0228092 | A1 | 7/2021 | Alp et al. |
| 2021/0298635 | A1* | 9/2021 | Addison .............. A61B 5/0077 |
| 2021/0316094 | A1 | 10/2021 | Kimm et al. |
| 2022/0088329 | A1* | 3/2022 | Handzsuj ................ A61B 5/742 |
| 2022/0105288 | A1 | 4/2022 | Beck et al. |

FOREIGN PATENT DOCUMENTS

| CN | 103619390 A | 3/2014 |
|---|---|---|
| JP | 2008516702 A | 5/2008 |
| JP | 2014518725 A | 8/2014 |
| WO | WO-2012/075493 A1 | 6/2012 |
| WO | WO-2012/162048 A1 | 11/2012 |
| WO | WO-2016/196837 A1 | 12/2016 |

OTHER PUBLICATIONS

International Search Report and Written Opinion dated Jan. 9, 2018, for application No. PCT/US2017/061162.

Japanese Patent Application No. 2019-524066, Notice of Reasons for Rejection, dated Jan. 18, 2023.

European Patent Application No. 17869396.6, Communication Pursuant to Article 94(3) EPC, dated Mar. 6, 2023.

\* cited by examiner

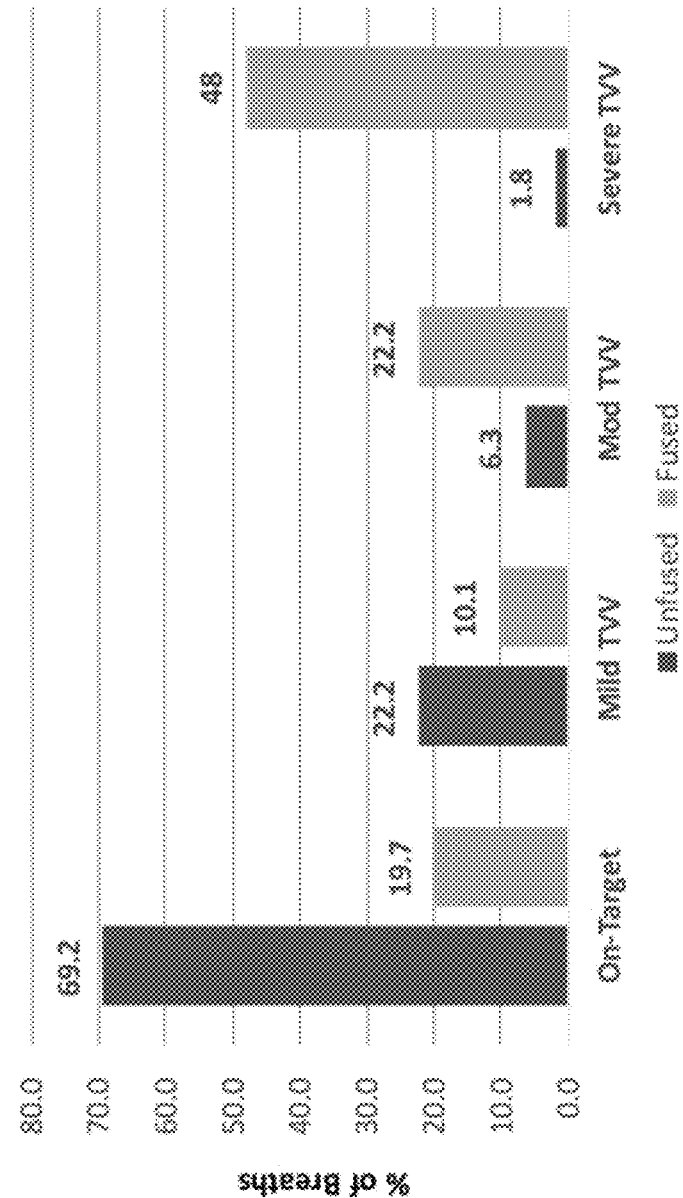

ated with government support under contract number 5K12HL108964-05 awarded by the National Heart, Lung, and Blood Institute. The government has certain rights in the invention.

RESUSCITATION AND VENTILATION ASYNCHRONY MONITOR

II. CROSS-REFERENCE TO RELATED APPLICATIONS

This application is a continuation of U.S. application Ser. No. 16/348,795, filed May 9, 2019, which was the national stage application under 35 U.S.C. § 371 of International Application No. PCT/US2017/061162, filed Nov. 10, 2017, which in turn claims the benefit of priority of U.S. Provisional Application Ser. No. 62/420,943, filed Nov. 11, 2016, the entire contents of each of which are incorporated herein by reference.

I. STATEMENT OF GOVERNMENT INTEREST

This invention was made with government support under contract number 5K12HL108964-05 awarded by the National Heart, Lung, and Blood Institute. The government has certain rights in the invention.

III. TECHNICAL FIELD

The present disclosure relates to patient resuscitation and ventilation monitoring systems.

IV. BACKGROUND

Acute respiratory failure is the most common reason for intensive care unit ("ICU") admission in the U.S. and is associated with an average in-hospital mortality of approximately 30% and $54 billion in attributable yearly costs. Airway management is an important aspect of emergency resuscitation and critical care. In turn, providing a proper ventilation rate and tidal volume is an important aspect of airway management. Proper ventilation rates and tidal volumes vary along with the overall patient size, e.g., height and weight, gender, and/or age. As such, pediatric airway management may be particularly difficult due to the wide range of heights and weights of pediatric patients.

During emergencies, first responders and clinicians commonly use bag valve masks ("BVM") or manual resuscitators for airway management. However, many first responders and clinicians inadvertently hyperventilate patients with BVMs or other resuscitation equipment, which may lead to serious complications. Hyperventilation decreases $CO_2$ in the body of a given patient, which results in alkalosis. Alkalosis impedes the patient's blood hemoglobin to bind to oxygen, which ultimately gives rise to potentially fatal conditions such as cerebral hypoxia and hyperventilation syndrome, which may lead to brain injury and patient mortality. Alkalosis also causes vasoconstriction, which may lead to decreased blood flow to the brain, and has been shown to result in worse outcomes in patients with traumatic brain injuries. Furthermore, inappropriate tidal volumes or the total volume of air that is given with each breath, may lead to barotrauma and the development of Acute Respiratory Distress Syndrome ("ARDS," a common and severe form of diffuse lung injury associated with increased morbidity and increased mortality of up to 50%).

Airway management may also be conducted via mechanical ventilation ("MV"), for example, when the patient is in the hospital. Similarly, MV devices may provide life-saving therapy, but if delivered improperly, can result in off-target ventilation, e.g., inappropriate respiratory rates and tidal volumes when not appropriately optimized for the patient's size or physiology, resulting in ventilator-induced lung injury ("VILI"), e.g., hypo- or hyper-ventilation as well as barotrauma. One of the principle mechanisms of VILI is known as volutrauma, whereby delivery of excessive tidal volumes ("TV", the volume delivered by the ventilator with each breath) results in pathologic alveolar distention, cellular injury, and the development of diffuse lung injury with many of the pathologic and clinical hallmarks of ARDS.

Excessive distention of lung tissue may result from inappropriately prescribed ventilator settings, excessive patient effort, or from subtypes of patient ventilator asynchrony ("PVA") that result in incomplete exhalation in between breaths, trapping gas in the lungs and further distending tissue. PVA is a type of off-target ventilation and may occur when a patient's respiratory demands are not matched by the ventilator's assistance, resulting in substantial patient distress, increased work of breathing, and the delivery of potentially injurious ventilation that may further promote lung injury. Randomized controlled trials in patients with ARDS suggest that targeting a low tidal volume ventilation ("LTVV") strategy of approximately 6 ml/kg of predicted body weight and controlling PVA improve survival although studies to date have not been able to separate the effects of excessive TV from those of PVA. Studies in ventilated patients without ARDS suggest that a LTVV strategy reduces the development of respiratory complications and hospital-acquired ARDS.

In addition, acute respiratory failure may be associated with a number of common syndromic phenotypes including ARDS, small-medium sized airway obstruction, and pneumothorax. ARDS is a clinical syndrome caused by a large number of insults to the lung including VILI. Optimal management of ARDS requires delivery of lung-protective mechanical ventilation. However, numerous studies have documented that clinicians consistently fail to recognize ARDS resulting in unnecessary patient exposure to injurious ventilator settings. Previous attempts to automate ARDS recognition have required coordinated analysis of data from multiple sources including electronic health record ("EHR") data and chest x-ray radiologist reports, making this approach impractical in settings where complex EHR interfacing and text mining technology are not available. Small-medium sized airway obstruction is commonly associated with acute exacerbations of asthma or smoking-related chronic obstruction pulmonary disease. Acute obstruction may also occur due to inhalation of smoke, aerosolized chemical irritants, and aspiration of gastric contents. A pneumothorax occurs when a lung collapses either spontaneously or as a result of trauma. The detection of a pneumothorax requires physical examination and/or radiographic imaging which may be difficult or impossible in resource limited or time sensitive situations.

Despite its high prevalence, cost, and associated suffering, MV remains difficult to study and no well-validated, widely available analytic or clinical decision support tools exist to facilitate patient-specific, precision management of MV. Waveform data from MV (and most other life support devices) are not generally available in the EHR, limiting the ability to develop analytic tools. MV data from clinical studies have typically been hand-recorded only a few times per day, representing a gross under-sampling of patients who routinely take more than 20,000 breaths per day, and most studies have been unable to collect and analyze the rich streams of ventilator waveform data ("VWD") used by clinicians at the bedside to diagnose and manage pathologic patient-ventilator interactions. Manual analysis of large volumes of physiologic waveform data is limited by its laborintensive nature, and recent data suggest that ICU clinicians perform poorly when asked to identify common forms of PVA through visual inspection of VWD, further supporting a need for standardized, automated analytic tools.

A number of small studies have collected VWD using intrusive, e.g., laptop computers, or non-scalable methods of data acquisition, using a variety of analytic approaches to classifying PVA from manual annotation to power spectral analysis to the application of proprietary waveform analysis software. These studies have demonstrated an important proof of concept, namely that MV waveform data are rich in historically unrecorded information pertinent to patient-ventilator interactions, and that analysis of PVA and other forms of "off target" ventilation ("OTV") may reveal associations with important clinical outcomes and processes of care. Studies to date have been limited by lack of access to ventilator data, intrusive data collection methods that may introduce observer bias and limit the feasibility of continuous longitudinal data collection, limited clinical validation of algorithm performance, inability to distinguish between OTV subtypes, and lack of defined analytic mechanisms to distinguish between true OTV events and waveform artifacts that may result in false positive event classification. As these issues are not unique to MV, the development of improved MV waveform analysis software serves as a generalizable use case for the challenges facing the broader development of healthcare "big data," e.g., specific analytics and decision support systems including barriers to data access, transmission, standardization, security, storage, and computation; incorporation of clinician-informed knowledge and heuristics into algorithms able to transform complex, high-volume raw data into actionable information while minimizing false alarms; and the development of well-engineered software solutions that allow extensibility, integration with other systems, and ultimately, provisioning of clinical decision support to the point of care.

It would therefore be desirable to provide improved systems and methods for airway management.

Specifically, it would be desirable to provide resuscitation and monitoring systems and methods that improve clinical decision support by determining acceptable ranges of measured airflow characteristics, determining specific types of off-target ventilation, and providing suggested corrective action in response to detected off-target ventilation types.

It would further be desirable to provide resuscitation and monitoring systems and methods that may automatically identify syndromic phenotypes with high levels of accuracy, without the usual need for advanced human clinical subspecialty diagnostic skills.

It would be also be desirable to have a device that works independently from any other devices or systems.

V. SUMMARY

The present disclosure overcomes the drawbacks of previously-known systems by providing systems and methods for improved resuscitation and ventilation monitoring, and enhanced clinical decision support.

One embodiment relates to a resuscitation and ventilation monitoring system. The system includes a processor having a memory a non-transitory computer-readable medium having instructions that, when executed by the processor, cause the processor to perform specified operations. For example, the processor may receive user input from a user, such as patient height, weight, gender, age. The processor may receive the user input via a measurement selector. The measurement selector may include a surrogate marker having numbers, letters, or colors. For example, the surrogate marker may include a plurality of colored options, wherein each of the plurality colored options correspond to colors and associated measurement increments defined by a Broselow Tape, and each of the colors and associated measurement increments defined by the Broselow Tape may correspond to a respective predetermined limit of the ventilation. The user input may also include user-defined settings for clinical decision support alarm thresholds and suggestions for corrective action.

The processor may also generate a ventilation signal indicative of a current mode of ventilation and associated ventilator settings based on at least one of airflow, pressure, oxygen, or carbon dioxide measurements received from an airflow meter and/or one or more sensors, e.g., a $CO_2$ sensor, an $O_2$ sensor, or a pressure sensor, in fluid communication with airflows exchanged with lungs of the patient. The processor may receive the airflow measurements from the airflow meter and/or one or more sensors via WiFi, Bluetooth, serial communication, or cellular communication. The processor may send raw ventilation data and derived information including clinical decision support via at least one of WiFi, Bluetooth, serial communication, or cellular communication, to one or more external destinations including, but not limited to, electronic medical record systems or telemedicine systems, and to one or more physiologic patient monitoring devices including, but not limited to, pulse oximeters, non-invasive blood pressure cuffs, invasive arterial blood pressure monitors, intracranial monitors, or cardiac and circulatory physiology monitors.

The processor may identify and filter out artifacts present in the ventilation signal, e.g., a suction event, a cough, or patient-ventilator disconnect. The processor may also determine whether a respiratory failure phenotype is present in the ventilation, e.g., acute respiratory distress syndrome, obstructive lung disease, or pneumothorax. Additionally, the processor may classify the monitored ventilation as either on-target or off-target based on whether the current mode of ventilation and associated ventilator settings are within a predetermined limit defined by the user input. For example, the predetermined limit of the ventilation defined by the user input may include a corresponding range of acceptable respiratory rates and tidal volumes. Further, the predetermined limit of the ventilation may include commonly accepted standards of practice based on the user input, specific to the patient.

If the processor determines that the ventilation is off-target, the processor may determine the type of off-target ventilation, e.g., tidal volume violation or PVA, and generate an alert if the ventilation is off-target. In one embodiment, the alert may be generated only if the off-target ventilation type exceeds the clinical decision support alarm thresholds. The alert may be, for example, an audio or visual alert. The processor suggests a corrective action to the user based on the off-target ventilation type via a user interface if the alert is generated. For example, if the processor determined that the off-target ventilation is a PVA, e.g., a double trigger asynchrony, breath stacking asynchrony, flow asynchrony, delayed termination asynchrony, early termination asynchrony, forced exhalation asynchrony, or ineffective trigger asynchrony, the suggested corrective action may be based on the PVA subtype, a frequency of the PVA, or a temporal pattern of the PVA. Additionally, if the processor determined that the off-target ventilation is a tidal volume violation, e.g., if a delivered inspiratory volume is off-target, the suggested corrective action may be based on the current mode of ventilation and associated ventilator settings. The suggested corrective action may be implementable by the user to adjust a manual bagging of the patient or ventilator settings of a mechanical ventilator.

The system may continuously analyze ventilation to determine changes in lung compliance over time and to identify pathological changes over time, e.g., acute respiratory distress syndrome, obstructive lung disease, or pneumothorax. For example, the system may continuously analyze $CO_2$ in exhaled breaths to at least identify at least one of inappropriate ventilation rates or pathology, or to predict outcome from cardiac arrest, or may continuously analyze the $O_2$ to identify when the $O_2$ content is either too high or too low for a current physiologic state, and to provide feedback to the user for changes in $O_2$ concentration.

The system may continuously analyze clinical data obtained via at least one of WiFi, Bluetooth, serial communication, or cellular communication from one or more external sources including, but not limited to, electronic medical records, and from one or more physiologic patient monitoring devices including, but not limited to, pulse oximeters, non-invasive blood pressure cuffs, invasive arterial blood pressure monitors, intracranial monitors, or cardiac and circulatory physiology monitors. The system may transmit raw ventilation data or higher order information derived from the resuscitation and ventilation monitoring system via at least one of WiFi, Bluetooth, serial communication, or cellular communication, to one or more external sources including, but not limited to, electronic medical record systems or telemedicine systems, and to other physiologic patient monitoring devices including, but not limited to, pulse oximeters, non-invasive blood pressure cuffs, invasive arterial blood pressure monitors, intracranial monitors, or cardiac and circulatory physiology monitors.

Another embodiment of the disclosure relates to a method of monitoring resuscitation and ventilation of a patient. The method includes receiving user input, e.g., patient height, weight, gender, or age, from a user via a measurement selector; generating a ventilation signal indicative of a current mode of ventilation and associated ventilator settings based on airflow measurements received from an airflow meter and/or one or more sensors in fluid communication with airflows exchanged with lungs of the patient; identifying and filtering out artifacts present in the ventilation signal; classifying the ventilation as either on-target or off-target based on whether the current mode of ventilation and associated ventilator settings are within a predetermined limit defined by the user input; determining off-target ventilation type and generating an alert if the ventilation is off-target; and suggesting corrective action based on the off-target ventilation type via a user interface if the alert is generated, wherein the suggested corrective action may be implementable by the user to adjust a manual bagging of the patient or ventilator settings of a mechanical ventilator. The method may also include determining whether a respiratory failure phenotype is present in the ventilation, and continuously analyzing ventilation to determine changes in lung compliance over time and to identify pathological changes over time, e.g., acute respiratory distress syndrome, obstructive lung disease, or pneumothorax.

The method may include continuously analyzing ventilation data in concert with clinical data derived from external sources to detect one or more pathologic states related to both the state of ventilation and to illnesses other than respiratory failure, such as when particular methods of ventilation delivery may contribute to the development of or worsening of circulatory shock, contribute to the development of or worsening of end-organ dysfunction, or is inadequate to meet the physiologic needs of a given acute illness, and prompting the operator to consider adjustment of ventilation settings.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

The system may work independently of any other devices or systems, and is not dependent upon other devices. Specifically, the device works with any type of mechanical ventilator or bag valve mask and does not require direct input from those devices.

VI. BRIEF DESCRIPTION OF THE DRAWINGS

The skilled artisan will understand that the drawings primarily are for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

FIGS. 11A and 11B illustrate the stratification of off-target breaths with and without tidal volume-fusion in accordance with the principles of the present disclosure.

Figure 1:
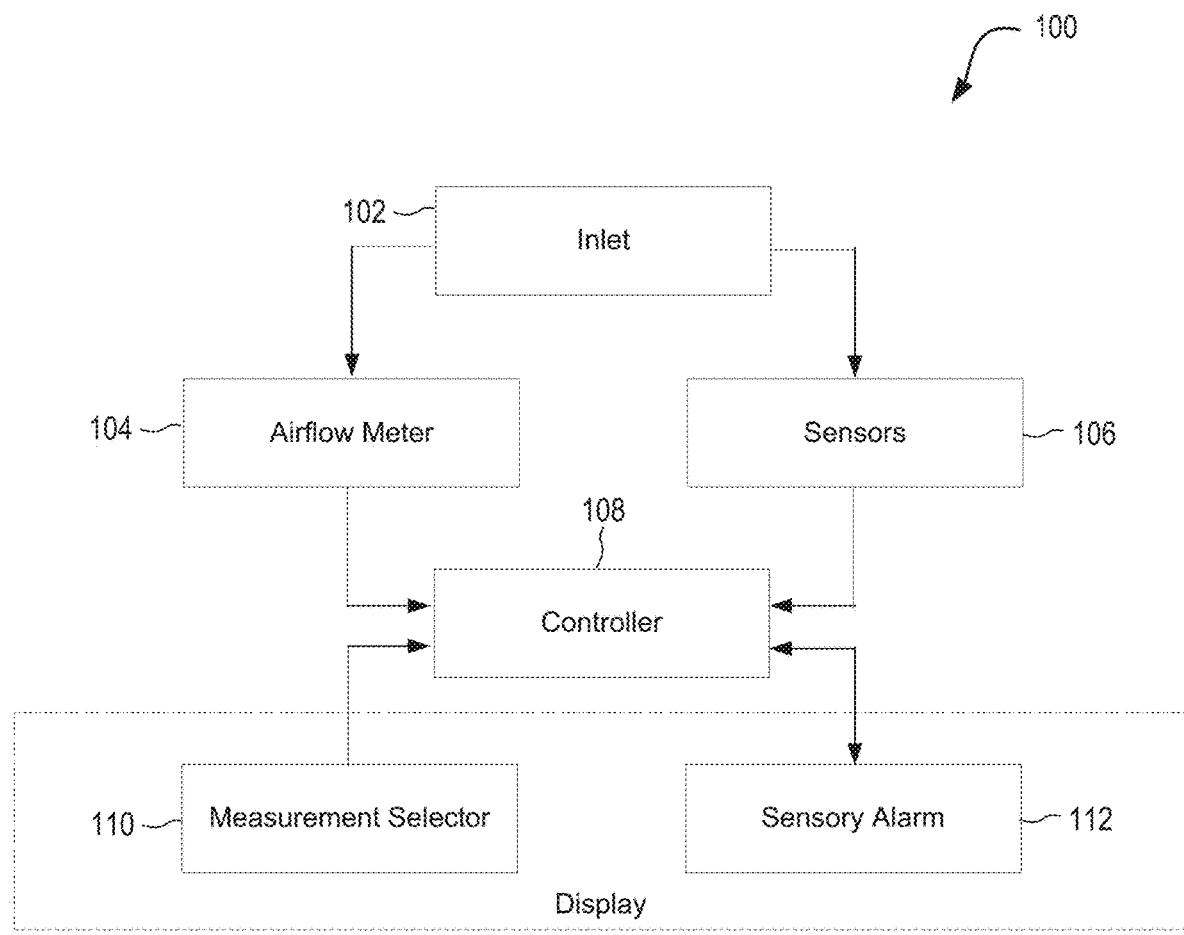
FIG. 1 is a schematic block diagram illustrating various features of a resuscitation and ventilation monitoring system, according to an example embodiment.

The features and advantages of the inventive concepts disclosed herein will become more apparent from the detailed description set forth below when taken in conjunction with the drawings.

VII. DETAILED DESCRIPTION

In the following detailed description, reference is made to the accompanying drawings, which form part of the present disclosure. The embodiments described in the drawings and description are intended to be exemplary and not limiting. As used herein, the term "example" means "serving as an example or illustration" and should not necessarily be construed as preferred or advantageous over other embodiments. Other embodiments may be utilized and modifications may be made without departing from the spirit or the scope of the subject matter presented herein. Aspects of the disclosure, as described and illustrated herein, may be arranged, combined, and designed in a variety of different configurations, all of which are explicitly contemplated and form part of this disclosure.

Unless otherwise defined, each technical or scientific term used herein has the same meaning as commonly understood by one of ordinary skill in the art to which this disclosure belongs. In accordance with the claims that follow and the disclosure provided herein, the following terms are defined with the following meanings, unless explicitly stated otherwise.

As used in the specification and claims, the singular form "a", "an" and "the" include both singular and plural references unless the context clearly dictates otherwise. For example, the term "a sensor" may include, and is contemplated to include, a plurality of sensors. At times, the claims and disclosure may include terms such as "a plurality," "one or more," or "at least one;" however, the absence of such terms is not intended to mean, and should not be interpreted to mean, that a plurality is not conceived.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a device or method consisting essentially of the elements as defined herein would not exclude other materials or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

"Component," as used herein, may refer to an individual unit or structure, or it may refer to a portion, feature, or section of a larger structure.

As used herein, "patient" shall mean any individual who receives resuscitation or ventilation treatment.

As used herein, a "user" shall refer to any individual who interacts with, or otherwise uses, any of the systems or devices disclosed herein. For example, a user may be a healthcare provider or healthcare technician, or a parent or guardian assisting or monitoring a patient.

Various embodiments disclosed herein are directed to a device that monitors various patient parameters such as respiration rate, tidal volumes, pressure, $CO_2$ levels, and $O_2$ levels during a resuscitation process. Although the present disclosure discusses respiration rate, tidal volumes, pressures, $CO_2$ levels, and $O_2$ levels in particular, one of skill in the relevant art would recognize that other embodiments may include devices that monitor other or additional parameters during patient resuscitation as well. The device may be incorporated with a bag valve mask (BVM), a bag and endotracheal tube, or other resuscitation equipment, such as a mechanical ventilator. The device includes adjustable control settings that correspond to dimensions, e.g., height and weight, gender, and/or age of a given patient, allowing the device to warn a user if proper ventilation rates and tidal volumes are not being delivered. Some embodiments of the device are particularly advantageous for use in airway management in children, incorporating a Broselow Tape system into the adjustable control settings. The Broselow Tape is a color coded tape corresponding to established ranges of pediatric patient heights. Each color is associated with proper ventilation techniques and other important medical procedures specific to a given size range (e.g., an appropriate ventilation rate and tidal volume for a given range of pediatric patient heights). In addition, some embodiments include a sensor that measures end tidal $CO_2$. Measuring end tidal $CO_2$ allows a user to determine whether the patient has a pulse (e.g., after cardiac arrest), monitor cardiac output and ventilations, and determine whether an associated endotracheal tube is properly disposed in a trachea (i.e., as opposed to an esophagus). The device may also include a sensor that measures oxygen concentration and/or a sensor that measures temperature of the airflow. In operation, a user may identify a color group their patient corresponds to on the Broselow Tape, and may adjust the control settings on the device corresponding to that color group. A user may also identify the height and sex of a patient and the device will adjust the control settings for that height and sex. The user may then start ventilating the patient; if the ventilation is too fast or too slow, an alarm system will be triggered, alerting the user to look at an associated display to see how the ventilation should be adjusted.

Referring now to FIG. 1, resuscitation and ventilation monitoring device 100 includes inlet 102, airflow meter 104, sensors 106, controller 108, measurement selector 110, and sensory alarm 112. In some arrangements, device 100 is incorporated into a BVM (e.g., disposed in line with airflows exchanged from a pump or bag) or some other resuscitation device, e.g., a bag and endotracheal tube or a mechanical ventilation device. Inlet 102 is configured to enable device 100 to be in fluid communication with the lungs of a patient. In some arrangements, inlet 102 is disposed in line with a conduit providing and receiving airflows with a patient mouth (e.g., disposed in line in a BVM). In some arrangements, inlet 102 is a mouthpiece configured to sealingly and removably engage the patient mouth. In some arrangements, inlet 102 is in fluid communication with airflows exchanged directly with a patient trachea. Consistent among these and other arrangements, inlet 102 enables airflows exchanged with the patient to pass through device 100.

Airflow meter 104 is configured to detect and measure respiration frequency and airflow volumes passing through inlet 102. Airflow meter 104 may include, for example, at least one of Fleisch type pneumotachometers, Lilly pneumotachometers, variable-orifice pneumotachometers, fixed-orifice pneumotachometers, hot wire anemometers, rotating vane spirometers, ultrasound-based pneumotachometer, or any other airflow meter known by one skilled in the art. As such, airflow meter 104 provides device 100 with data corresponding to a patient respiratory rate and tidal volumes. For example, the airflow meter 104 may be configured to measure respiratory rates ranging from 1-75 breaths per minute ("bpm") and tidal volumes of 5-5,000 mL. In addition, airflow meter 104 may be configured to detect, measure, and compare the volume of an inhaled breath versus an exhaled breath of the patient within a breath cycle, such that the difference, i.e., Δ, may then be displayed on the user interface of device 100. Similarly, sensors 106 may include, for example, a $CO_2$ sensor configured to detect and measure $CO_2$ levels in airflows passing through inlet 102. For example, sensors 106 may be configured to measure $CO_2$ levels ranging from 0-99 mmHg. Sensors 106 may include a pressure sensor that measures the pressure within the airflow passing through the device. Sensors 106 may include an $O_2$ sensor configured to detect and measure $O_2$ levels in airflows passing through inlet 102. Additionally or alternatively, sensors 106 may include a temperature sensor configured to detect and measure the temperature of the airflow passing through inlet 102, as well as the humidity of the airflow passing through inlet 102.

Measurement selector 110 is an input component that allows the user to provide device 100 with information relating to the size, gender, and/or age of the patient. In some arrangements, measurement selector 110 includes a plurality of preset buttons, toggles, switches, or other mechanically or digitally interactive components corresponding to pre-set increments of patient sizes (e.g., a surrogate marker including colors corresponding to colors of the Broselow Tape or direct measurement of the patient). In other arrangements, measurement selector 110 allows the user to manually enter specific patient size measurements, gender, and/or ages (e.g., a keyboard or a numerical pad, as disposed on a mechanical set of keys or a digital touchscreen), thereby allowing for a greater level of granularity.

Sensory alarm 112 is an output component configured to communicate with the user when at least one parameter (e.g., measured respiratory rate, tidal volume, pressure, difference in inhaled and exhaled volumes, $CO_2$ levels, or $O_2$ levels) is above or below acceptable levels (i.e., as determined by patient size, gender, and/or age information provided through measurement selector 110). In some arrangements, sensory alarm 112 is configured to provide the user with auditory signals (e.g., a beep, a tone, etc.). In some arrangements, sensory alarm 112 is configured to provide the user with visual signals (e.g., an illuminated light such as a lit LED or filament bub, or a message on a digital display, etc.).

Further, in some arrangements, sensory alarm 112 and/or measurement selector 112 may be incorporated into display 114. Display 114 is a digital screen configured to provide information to a user (e.g., an LCD screen). In some such arrangements, display 114 may include a touchscreen component disposed on device 100, allowing the user to both view measurement information (e.g., respiratory rates, tidal volumes, ventilation waveforms, pressure, difference in inhaled and exhaled volumes, temperatures, $CO_2$ levels, $O_2$ levels) and acceptable ranges of such measurements, as well as provide device 100 with measurement information (e.g., patient sizes, patient gender, patient ages, Broselow Tape color selections, etc.). The measurement information may include color coded alarms to indicate if the ventilation is on-target or off-target, and percentages of breaths that are off-target. Sensory alarm 112 and/or display 114 may be part of a separate device remote from device 100, such that device 100 sends information to the sensory alarm of the separate remote device when at least one parameter is above or below an acceptable level to communicate with the user via auditory or visual signals. The remote device may further include a user interface having, for example, a measurement selector as described above for inputting patient information. Communication between device 100 and the user interface of the separate remote device may occur across multiple platforms, e.g., WiFi, Bluetooth, serial communication, optical communication, and cellular communication. In addition, the communication between device 100 and the user interface of the separate remote device may occur across a variety of ranges, e.g., short (feet) or distant (miles).

Controller 108 includes data processing and non-transient storage hardware and associated logics to perform various functions described herein. Data processing hardware, e.g., a processor, may include and/or be coupled to non-transient storage hardware having instructions, e.g., algorithms, stored thereon that when executed by the processor cause the processor, and thereby controller 108, to perform various functions. For example, controller 108 may be configured to receive a user input from measurement selector 110 corresponding to a patient size (e.g., a Broselow Tape color, or numerical measurements of height and weight), patient gender, and/or patient age. Controller 108 may then determine or retrieve acceptable measurement ranges for the patient size, gender, and/or age (e.g., as stored in a non-transient storage medium such as a flash drive, or as determined by a measurement calculation logic). Airflows from the patient may then pass through inlet 102, causing airflow meter 104 and sensors 106 to provide controller 108 with airflow measurements. The data processing hardware of controller 108 may calculate or process corresponding respiratory rates, tidal volumes, pressures, differences in inhaled and exhaled volumes, $CO_2$ and $O_2$ levels, and temperatures upon execution of the instructions stored thereon, compare those values with the acceptable measurement ranges, and cause sensory alarm 112 to alert the user if the airflow measurements fall outside the acceptable measurement ranges. The processed information may be in the form of pressure and/or flow waveforms, such that the waveforms are displayed on the user interface for observation. Controller 108 may store airflow measurement information and/or calculated or processed information in the non-transitory storage medium, such that the stored information may be downloaded at a later time for analysis. Additionally, device 100 may continuously analyze ventilation to determine changes in lung compliance over time and to identify pathological changes over time, e.g., acute respiratory distress syndrome, obstructive lung disease, or pneumothorax.

Device 100 may be configured to work within a network of devices and user interfaces. For example, device 100 may be placed in line to measure flow, and process and send information to remote locations where a remote user device having a user interface, e.g., a tablet, phone, computer, or a "heads up display" such as Google glasses, communicates the information to the user. In some such arrangements, multiple devices may send information to a single user interface. Accordingly, calculations may be executed by controller 108 on device 100 itself, or raw data streams from airflow meter 104 and sensors 106 may be sent to a remote controller of a separate device where calculations are executed and displayed to the user. Communication between device 100 and the user interface of the separate remote device may occur across multiple platforms, e.g., WiFi, Bluetooth, serial communication, and cellular communication. In addition, the communication between device 100 and the user interface of the separate remote device may occur across a variety of ranges, e.g., short (feet) or distant (miles). Components of the device and several arrangements thereof are discussed in more detail below.

Figure 2A:
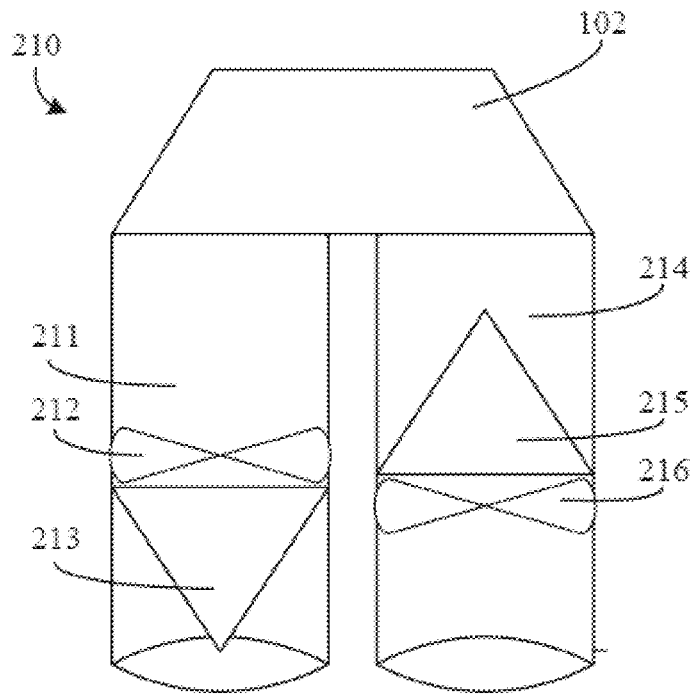
FIGS. 2A-2D illustrate various arrangements of an airflow meter.

Referring now to FIG. 2A, first airflow meter arrangement 210 incorporates the use of fans, and includes outflow chamber 211 and inflow chamber 214. Outflow chamber 211 includes one-way outflow valve 213 and outflow fan 212. In turn, inflow chamber 214 includes a corresponding one-way inflow valve 215 and inflow fan 216. Each of outflow chamber 211 and inflow chamber 214 are in fluid communication with inlet 102, which is in line with airflows exchanged with the lungs of a patient.

In first airflow meter arrangement 210, air pumped into the patient's lungs flows through inflow chamber 214, and air withdrawn out of the patient's lungs flows through outflow chamber 211, as a result of each respective one-way valve. As air flows through a given chamber (e.g., outflow chamber 211), the associated fan (e.g., outflow fan 212) will spin. Each fan includes a magnet attached to a fan axle, generating a current while the fan spins. The generated current may pass over a fan resistor where a voltage may be measured. As such, a time between output voltage peaks may be used to determine a ventilation rate. The area underneath a voltage curve of inflow fan 216 corresponds to the volume of air delivered to the lungs of the patient, and the area underneath a voltage curve of outflow fan 212 corresponds to the volume of air withdrawn from the lungs of the patient. The difference between the volumes of air delivered and withdrawn (i.e., passing through inflow chamber 214 and outflow chamber 211, respectively) may indicate the presence and extent of any air leaks (e.g., in the device 100 itself, at a ventilation mask, at an endotracheal tube, etc.).

Outflow fan 212 and inflow fan 216 should be comprised of materials that may survive temperature and moisture conditions present during patient resuscitation. Acceptable fan materials include, for example: glass reinforced polypropylene (PPG); glass reinforced polyamide (PAG—Nylon); glass reinforced polyamide, industrial quality (PAGI); electro anti-static glass reinforced (PAGAS—Nylon); vibration stabilized glass reinforced polyamide (PAGST—"Super Tuff" Nylon); and aluminum, EN AC-AL SI12CU1 (FE) (AL).

Figure 2B:
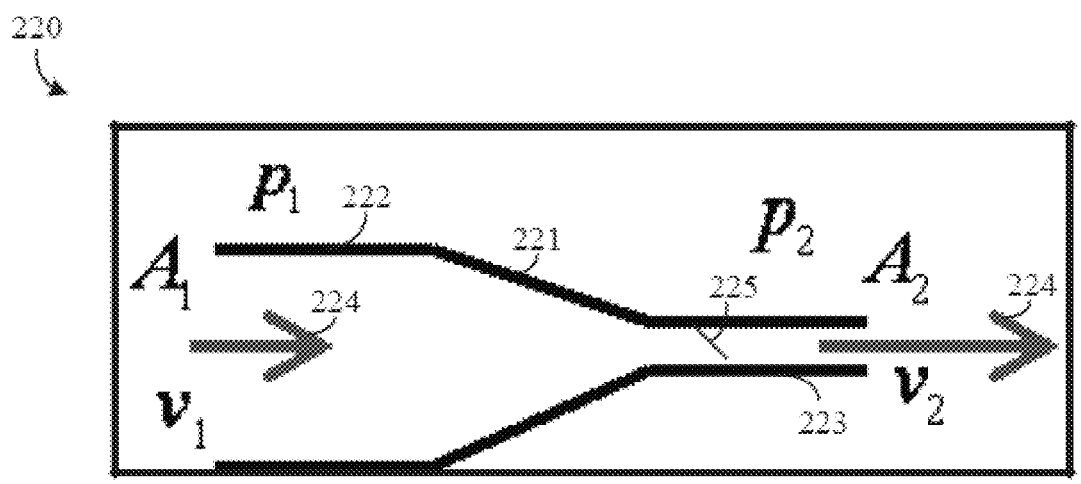

Referring now to FIG. 2B, second airflow meter arrangement 220 incorporates the use of a volumetric flowmeter. Second airflow meter arrangement 220 includes airflow conduit 221 with upstream end 222 having a first area and downstream end 223 having a smaller second area (i.e., relative to the first area). Airflow 224 (e.g., traveling to or from the lungs of a patient) travels from upstream end 222 to downstream end 223. Given the difference in area, airflow 224 exhibits a lower first velocity and a lower first pressure at upstream end 222, and a corresponding higher second velocity and a higher second pressure at downstream end 223. In one arrangement, articulating pressure flap 225 is disposed perpendicularly to the direction of airflow 224 in downstream end 223. Pressure flap 225 is configured to pivot across a range of motion corresponding to an airflow pressure exerted upon it, thereby measuring the pressure at downstream end 223. As such, in second airflow meter arrangement 220, the respiration rate may be determined from the oscillation of pressure flap 225, and the tidal volume may be determined from the known values (e.g., the first and second volume) and measured values (e.g., the first and second pressure and the first and second velocity) as applied to Bernoulli's equation:

$$\frac{1}{2}\rho v^2 + \rho gz + p = \text{constant} \quad v_2^2 = v_1^2 \left(\frac{\rho 1 A 1}{\rho 2 A 2}\right)^2$$

where $\rho$, v, and p represent density, velocity and pressure of the airflow, respectively. Pressure flap 225 may also be configured to be parallel to the wall of the sensor at downstream end 223. Another pressure sensor may be configured to parallel to the wall at upstream end 222. These two pressure sensors may be used to calculate a differential pressure across the sensor and to calculate flow using the Bernoulli equation.

Figure 2C:
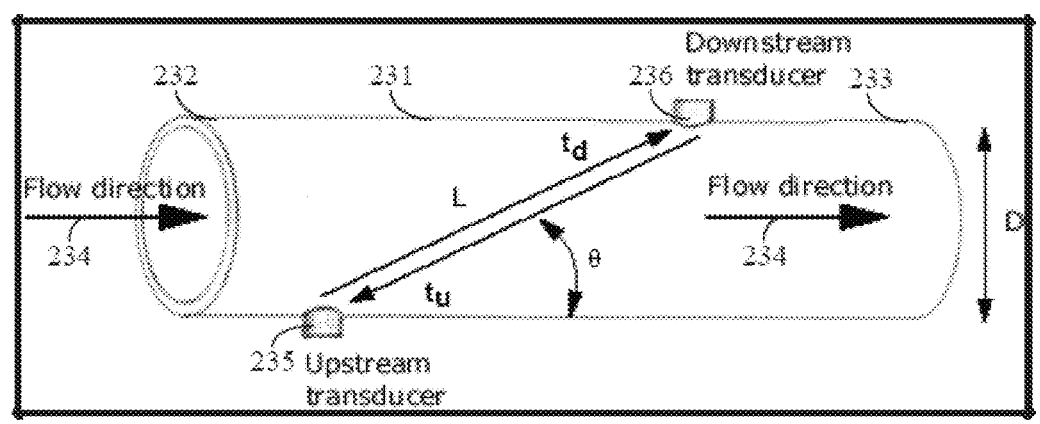

Referring now to FIG. 2C, third airflow meter arrangement 230 incorporates ultrasonic transducers to measure tidal volumes and respiratory rates. Third airflow meter arrangement 230 includes airflow conduit 231 having upstream end 232 and downstream end 233. Airflow 234 (e.g., traveling to or from the lungs of a patient) travels from upstream end 232 to downstream end 233. First ultrasonic transducer 235 is disposed in airflow conduit 231 towards upstream end 232, and second ultrasonic transducer 236 is disposed in airflow conduit 231 towards downstream end 233 (i.e., relative to first ultrasonic transducer 235). Each transducer emits and receives sound in alternating directions. When airflow 234 is present in airflow conduit 231, the time it takes for acoustic waves to travel from first ultrasonic transducer 235 to second ultrasonic transducer 236, to (i.e., acoustic waves traveling with airflow 234), is shorter than from second ultrasonic transducer 236 to first ultrasonic transducer 235, $t_u$ (i.e., acoustic waves traveling against airflow 234). This difference in time, $\Delta t$, is proportional to the velocity of airflow 234, and airflow volume may also be calculated in the following manner:

Mathematical Model $$V = L^2 \Delta t / 2 X t_u t_d$$

V: Flow velocity
L: Distance between the transducers
X: Projected length of the path along the valve (X=L cos θ)
$t_u$: time for wave signal to travel upstream
$t_d$: time for the wave signal to travel downstream Volumetric Flow $$Q = VA$$

The transit time of each sound pulse from each transducer may be precisely measured with a digital clock.

In third airflow meter arrangement 230, airflow conduit 231 may be disposable since it may be configured to have no sensor elements exposed to airflow 234 and/or to have no moving parts. In such an arrangement, airflow conduit 231 acts only as a hygienic shield and is transparent to the ultrasonic pulses traveling between the transducers. Potential advantages of third airflow meter arrangement 230 include sensor elements that are not directly in contact with gas flow, and measurement data that is relatively insensitive to other factors such as temperature, pressure, density and viscosity of fluids.

Figure 2D:
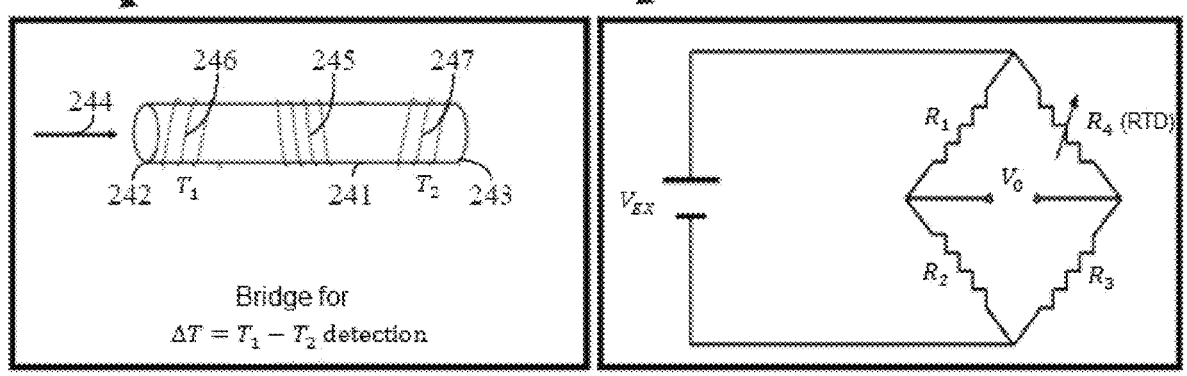

Referring now to FIG. 2D, fourth airflow meter arrangement 240 incorporates mass airflow sensors. Fourth airflow meter arrangement 240 includes airflow conduit 241 having upstream end 242 and downstream end 243. Airflow 244 (e.g., traveling to or from the lungs of a patient) travels from upstream end 242 to downstream end 233. In addition, heater circuit 245 is disposed between upstream temperature sensor 246 and downstream temperature sensor 247, each of which are annularly disposed about airflow conduit 241.

In operation, a predetermined amount of heat is applied to heater circuit 245. Upstream temperature sensor 246 and downstream temperature sensor 247 are each not directly heated, and as such, act as reference points to heater circuit 245. When there is no flow through airflow conduit 241, the differences in temperatures between heater circuit 245 and each of upstream temperature sensor 246 and downstream temperature sensor 247 are at their greatest. As airflow 244 flows through airflow conduit 241, heater circuit 245 cools and the differences in temperatures between heater circuit 245 and each of upstream temperature sensor 246 and downstream temperature sensor 247 decreases. In addition, as upstream temperature sensor 246 and downstream temperature sensor 247 are disposed on either side of heater circuit 245, resulting temperature differentials may indicate the direction of airflow 244 as well. Alternating directions of airflow 244 may thus be detected and give rise to respiration rates.

In some arrangements, dual Wheatstone bridge system 248 is disposed on airflow conduit 241 and incorporates heater circuit 241, upstream temperature sensor 246, and downstream temperature sensor 247 as a resistance-temperature detector ("RTD"). In an RTD, one of the resistance values will be dependent on the measured temperature differential. The output of the RTD is relatively linear with temperature, giving rise to a ratiometric output voltage that directly corresponds to the differential voltage across the Wheatstone bridge that is proportional to the mass flow.

Figure 3A:
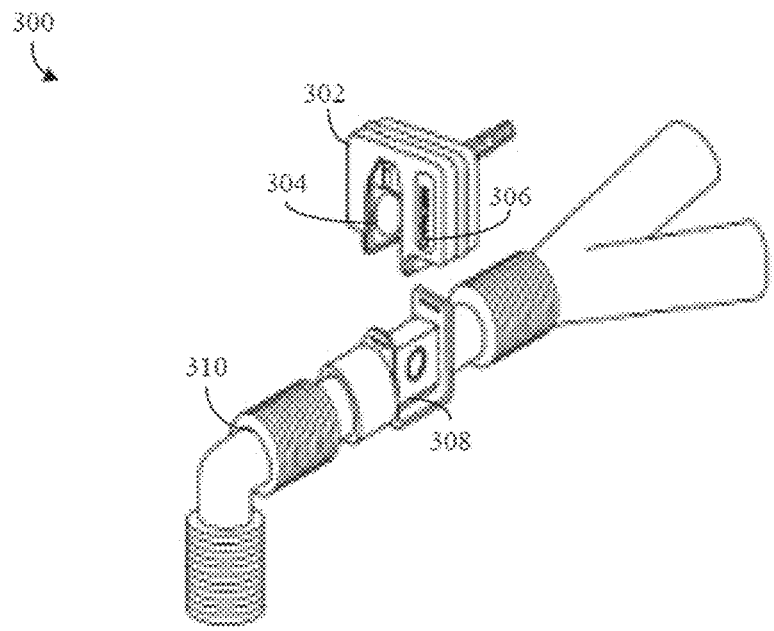
FIG. 3A illustrates an example arrangement of a $CO_2$ sensor.
Figure 3B:
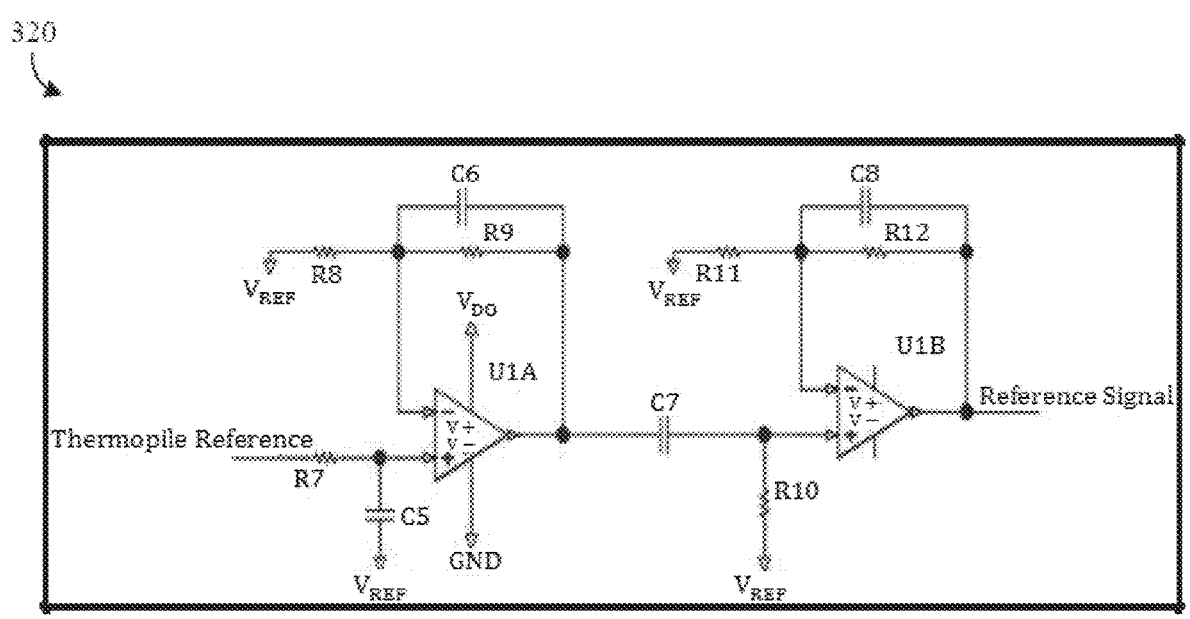
FIG. 3B is a schematic diagram illustrating an example arrangement of a band pass filter.

Although four examples of airflow meter 104 have been provided in FIGS. 2A-2D, one of skill in the relevant art would recognize that other arrangements are possible. For example, airflow meter 104 may be implemented using other IR spectrometers, Fleisch type pneumotachometers, Lilly pneumotachometers, variable-orifice pneumotachometers, fixed-orifice pneumotachometers, hot wire anemometers, rotating vane spirometers, or ultrasound-based pneumotachometer Referring now to FIG. 3A, example sensor arrangement 300 corresponding to sensors 106 incorporates IR spectrometry. Sensor arrangement 300 includes sensor housing 302, which serves as a foundation upon which sensor components are attached. IR source 304 is disposed in sensor housing 302 opposite IR detector 306. IR source 304 provides infrared light across an airflow exchanged with the lungs of a patient and to IR detector 306. In some arrangements, IR source 304 includes an IR filter configured to narrow the range of wavelengths passing through the airflow. Further, in some arrangements, a band-pass filter may be disposed within sensor housing 302 to remove all other wavelengths outside the absorption range of $CO_2$ or $O_2$ depending on the type of sensor (e.g., circuitry component 320 as shown in FIG. 3B). IR detector 306 may include a thermopile with a built-in filter correspondingly configured to detect IR intensity after passing through the airflow, and may thus determine the amount of $CO_2$ and $O_2$ in the airflow. Sensor housing 302 may be configured to engage corresponding adapter slot 308 disposed in line with airflow conduit 310. Adapter slot 308 is configured to allow IR source 304 to transmit infrared light across an airflow within airflow conduit 310 and to IR detector 306. In some arrangements, airflow conduit 310 includes one or more filters configured to remove water from the airflow.

Figure 4A:
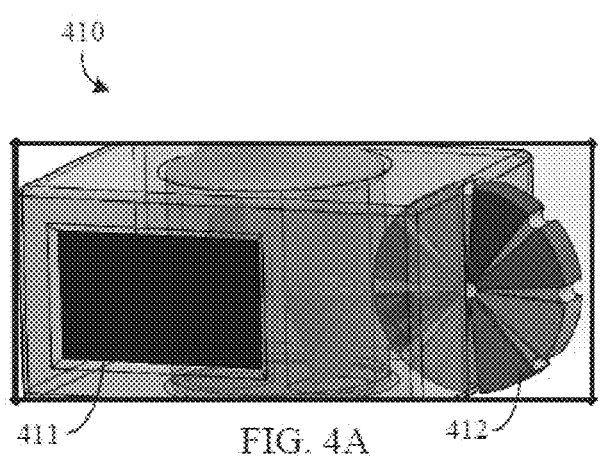
FIGS. 4A-4C illustrate various arrangements of a measurement selector.

Referring now to FIG. 4A, first arrangement 410 of measurement selector 110 is shown. First arrangement 410 includes display 411 (e.g., display 114). Display 411 is a digital screen configured to provide a user with information relating to the operation of resuscitation and ventilation monitoring device 100 (e.g., measurement information, acceptable measurement ranges, etc.). In some arrangements, display 411 includes an input aspect such as a touchscreen or an associated keypad or keyboard. As such, in some such arrangements, the user may be able to manually enter precise patient measurements (e.g., a specific height and weight), gender, and/or age using display 411. Device 100 may be configured to use the manually entered patient measurements to categorize the patient in an appropriate group (e.g., one of the Broselow Tape colors, corresponding to a height and weight range that includes the specific height and weight entered), or to generate acceptable measurement ranges tailored to the patient's specific height and weight, gender, and/or age.

First arrangement 410 also includes dial 412 with selectable colors corresponding to the Broselow Tape. The Broselow Tape assigns different colors according to the size (e.g., height and weight) of a patient, which may be represented by corresponding notched sections on dial 412. When the user selects a color using dial 412, device 100 will tell the user the appropriate ventilation rate and will alarm the user when ventilation is inadequate (e.g., via display 411). Pediatricians and other medical personnel may already be familiar with how the Broselow Tape is used, and as such, using dial 412 may be faster and easier than using display 411 to manually enter the height, sex, and weight values of a given patient. In addition to sections corresponding to colors of the Broselow Tape, dial 412 may include one or more notched sections that correspond to one or more adult sizes.

Figure 4B:
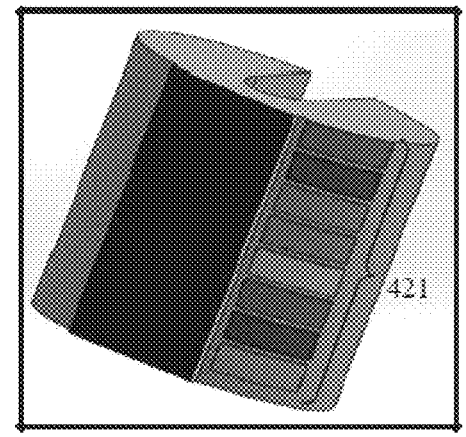
Figure 4C:
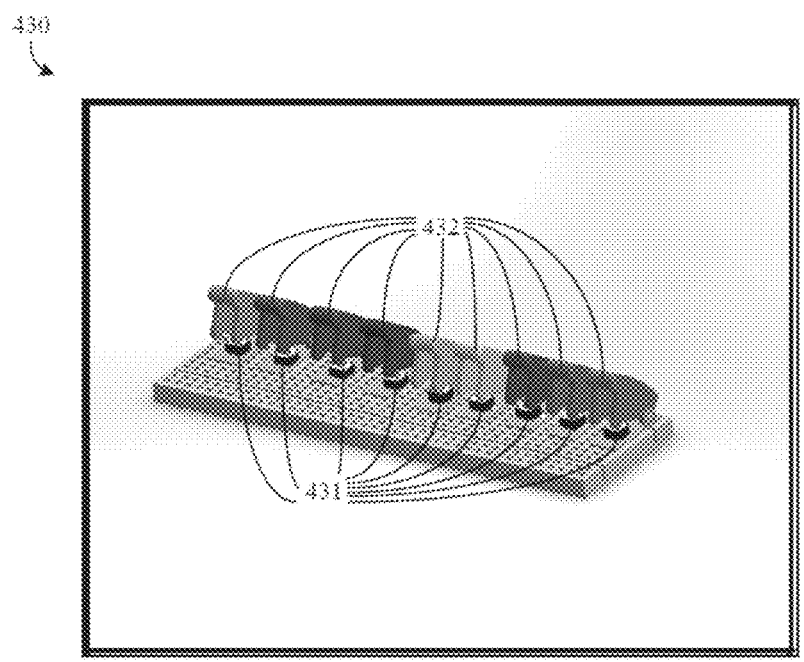

Referring now to FIG. 4B, as shown in second arrangement 420 of measurement selector 110, Broselow Tape settings may be assigned to some or all of plurality of pushbuttons 421 (i.e., instead of dial 412 of FIG. 4A). In addition, plurality of pushbuttons 421 may also include labels of heights corresponding to the Broselow Tape colors so a user may quickly select a correct setting during resuscitation. Further, as shown in third arrangement 430 of measurement selector 110, plurality of pushbuttons 431 may be protected from inadvertent actuation by corresponding plurality of switch covers 432.

Figure 5A:
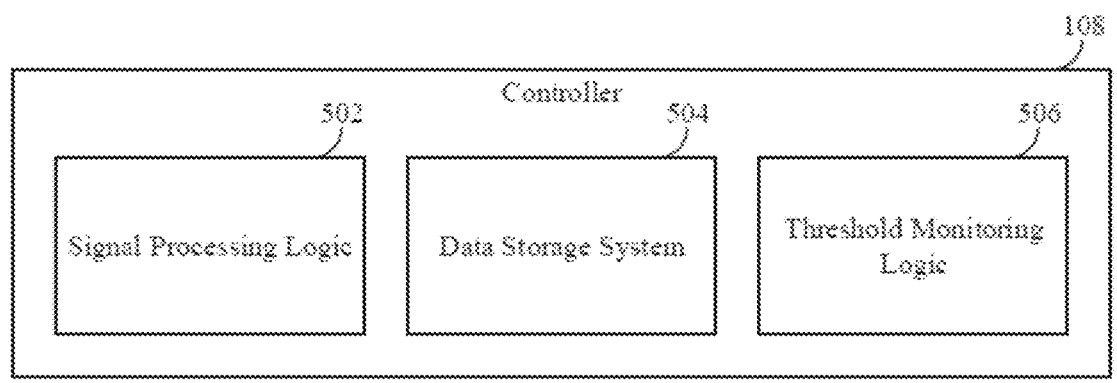
FIG. 5A is a schematic block diagram illustrating various features of a controller.

Referring now to FIG. 5A, controller 108 includes signal processing logic 502, data storage system 504, and threshold monitoring logic 506. Signal processing logic 502 is configured to receive measurement data from airflow meter 104 and sensors 106. In one aspect, signal processing logic 502 is configured to receive measured $CO_2$ levels from sensors 106, and route the measured $CO_2$ levels to threshold monitoring logic 506. In another aspect, signal processing logic 502 is configured to receive measured $O_2$ levels from sensors 106, and route the measured $O_2$ levels to threshold monitoring logic 506. In yet another aspect, signal processing logic 502 is configured to receive measured temperatures from sensors 106, and route the measured temperatures to threshold monitoring logic 506. In yet another aspect, signal processing logic 502 is configured to receive measured airflow data from airflow meter 104, and route the airflow data to threshold monitoring logic 506. In yet another aspect, signal processing logic 502 is configured to receive measured pressure from sensors 106, and route the pressure data to threshold monitoring logic 506. In another aspect, signal processing logic 502 may be configured to receive measured air humidity from sensors 106, and to route the measured humidity measurement to threshold monitoring logic 506. In some arrangements, signal processing logic 502 is further configured to calculate respiration rates, tidal volumes, and the difference in inhaled and exhaled volume, e.g., A, from the measured airflow data (e.g., as discussed above with respect to FIGS. 2A-2D), and forward the respiration rates, tidal volumes, and A to threshold monitoring logic 506.

Figure 5B:
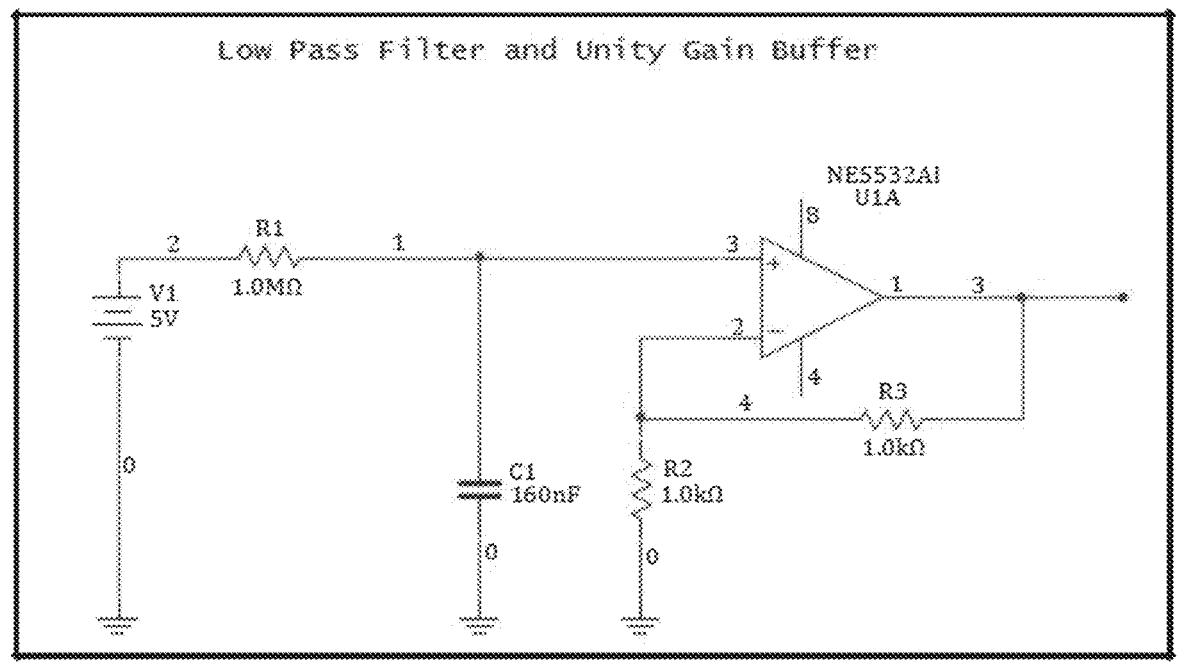
FIG. 5B is a schematic diagram illustrating an example arrangement of a low pass filter.

In some arrangements, the output voltage generated by sensors at airflow meter 104 and sensors 106 may be in the range of about 5 Vdc±0.36 Vdc at 200 SLPM (standard liters per minute), and as such, no signal amplification is required. The frequency range corresponding to human respiratory rate may be in the range of about 0.1 to 1.0 Hz. Hence, a low pass filter followed by a unity gain voltage buffer with the specifications (e.g., as shown by low pass filter circuit 510 in FIG. 5B) may be used as part of signal processing logic 502 to eliminate the noise and adjust the output impedance. Further, in some arrangements, the input signal from the sensors is analog and signal processing logic 502 may also be configured to perform an analog to digital conversion (e.g., 8/16-channel, 10, 12, or 16-bit ADC).

Data storage system 504 is an on-board storage medium configured to retrievably maintain data, for example, data corresponding to ranges of acceptable $CO_2$ levels, $O_2$ levels, tidal volumes, respiration rates, pressures, and differences in inhaled and exhaled volume for a plurality of patient sizes. In some arrangements, the ranges are organized by categories corresponding to colors of the Broselow Tape. In some arrangements, acceptable ranges for adults are stored on data storage system 504 as well. Further, in some arrangements, data storage system 504 may include calculation algorithms for determining specific ranges for $CO_2$ levels, $O_2$ levels, tidal volumes, respiration rates, and differences in inhaled and exhaled volume for specific patient heights and weights, gender, and/or age. Data storage system 504 may store the data so that the stored data may be downloaded at a later time for analysis.

In some arrangements, data storage system 504 includes calculation algorithms to adjust pressure sensor readings to compensate for temperature or humidity as measured by sensor 106.

Threshold monitoring logic 506 allows controller 108 to interface with a user of device 100. For example, threshold monitoring logic 506 may be configured to receive a user input from measurement selector 110 corresponding to a patient's height and weight (e.g., a Broselow Tape color, or a specific height and weight), gender, and/or age. Threshold monitoring logic 506 may then retrieve appropriate respiratory rate, tidal volume, difference in inhaled and exhaled volume, $CO_2$ level, and $O_2$ level ranges from data storage system 504. Where a specific patient height and weight, gender, and/or age is provided in the user input, threshold monitory logic 506 may retrieve and execute a calculation algorithm from data storage system 504 to determine appropriate ranges. In some arrangements, threshold monitoring logic 506 causes a display (e.g., display 114) to present the user input and the ranges to the user.

Threshold monitoring logic 506 receives measurement data (e.g., respiratory rates, tidal volumes, pressures, differences in inhaled and exhaled volume, $CO_2$ levels, and $O_2$ levels) from signal processing logic 502 and compares the measurement data with the respiratory rate, tidal volume, difference in inhaled and exhaled volume, $CO_2$ level, and $O_2$ level ranges appropriate for the patient's size, gender, and/or age. In some arrangements, if at least one these measurement data types falls above or below a respective range, threshold monitoring logic 506 causes sensory alarm 112 to notify the user that ventilation currently being applied is not appropriate for the patient's size, gender, and/or age. In some such arrangements, the threshold monitoring logic causes display 114 to provide the user with information relating to current measurement data and whether the current measurement data falls above or below an appropriate range.

Figure 6:
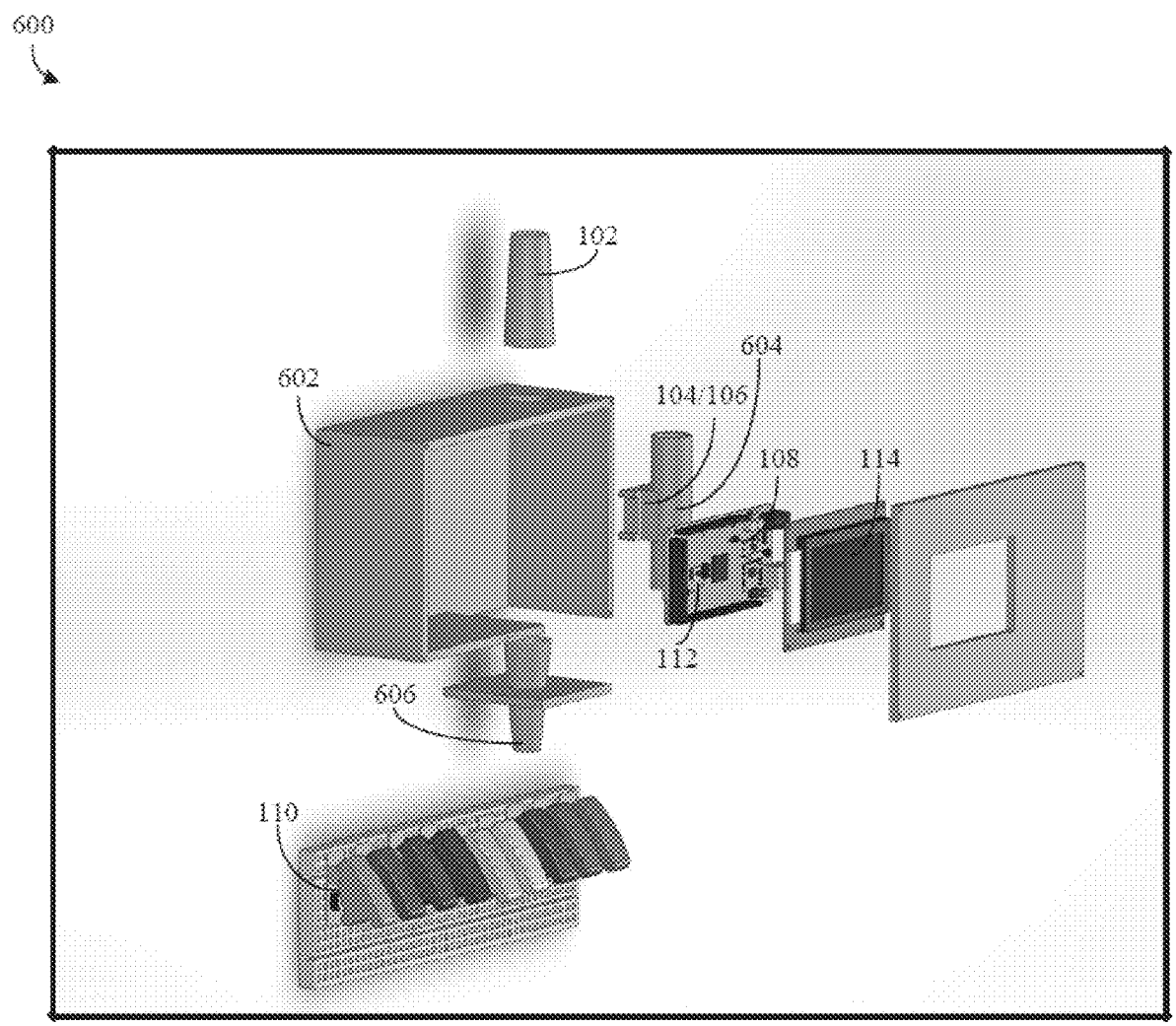
FIG. 6 is an exploded view of an example embodiment of the resuscitation and ventilation monitoring device of FIG. 1.

Referring now to FIG. 6, example embodiment 600 of device 100 is shown. In example embodiment 600, inlet 102 is communicatively engaged to airflow conduit 604, which in turn is communicatively engaged to outlet 606. Inlet 102 may be further engaged to a mouthpiece or other adapter configured to removably engage a patient airway. Outlet 606 may be engaged to a pressure manipulation device, for example a BVM or a mechanical ventilator. Airflow conduit 604 houses airflow meter 104 and sensors 106, and bridges inlet 102 to outlet 606.

In example embodiment 600, inlet 102 and outlet 606 are disposed on the exterior of enclosure 602, while airflow conduit 604 is disposed in the interior of enclosure 602. Enclosure 602 is a protective housing and foundation for various components of device 100. Enclosure 602 may be made up of any several types of materials (e.g., plastic, acrylic, metal, or alloys thereof) and may be assembled in various ways (e.g., snapped together at a plurality of pegs and slots, fastened via bolts or screws, glued, etc.).

Controller 108 is disposed within enclosure 602. Controller 108 may be embodied as, for example, an Arduino Mega 2560 8-bit microcontroller or other suitable programmable microcontroller. In addition to data processing hardware, the Arduino Mega 2560 includes 128 KB of flash memory (i.e., data storage system 504). Further, in example embodiment 600, controller 108 includes sensory alarm 112 mounted on an associated circuit board, for example as a flashing LED and/or a speaker. Controller 108 may also be embodied as a custom microcontroller for data processing with data storage system 504.

Example embodiment 600 further includes display 114 embodied as a digital (e.g., LCD) screen. Display 114 is electrically engaged to controller 108, and as such may be configured to provide a user with measurement, range, waveforms, and alert information.

Figure 7:
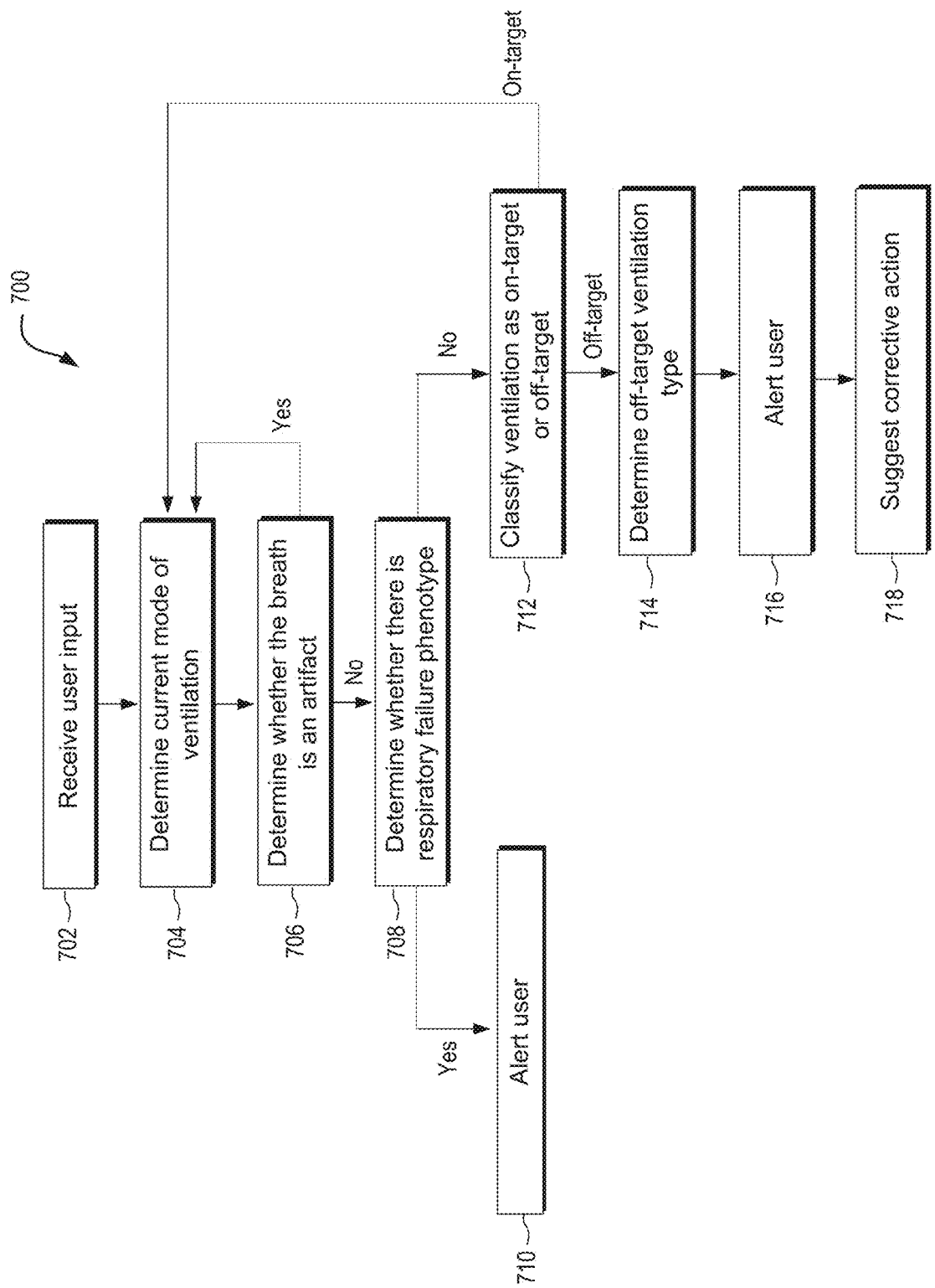
FIG. 7 illustrates a flow chart depicting the actions performed by the processor of a ventilation system in accordance with the principles of the present disclosure.

Referring now to FIG. 7, flow chart 700 illustrates the actions performed by controller 108 of device 100 coupled to a ventilator. The controller identifies ideal ventilation conditions using preset definitions followed by comparisons to current ventilation measurements to provide clinical decision support. Initially, at step 702, controller 108 receives user input from a user, e.g., patient or clinician, via measurement selector 110. For example, the user may input patient information including height, weight, gender, and age. For adult patients, height may be entered in metric or English measurement units using a tape measurer or reported height. Pediatric height may be entered using colors based on the Broselow tape, or in metric or English measurement units using a tape measurer or reported height. Additionally, the user may input user-defined settings for clinical decision support alarm thresholds and suggestions for corrective action. From the inputted information, controller 108 may determine ideal ventilation conditions using preset definitions stored in the memory of controller 108, e.g., data storage system 504. The ideal ventilation conditions may be commonly accepted standards of practice based on the inputted information.

Next, at step 704, controller 108 receives airflow measurements from airflow meter 104 and/or one or more sensors 106 as described above, and automatically calculates the current mode of ventilator and associated ventilator settings from pressure and flow waveforms derived from the airflow measurements. The shape of the pressure waveform and the shape of the flow waveform may be analyzed to determine the type of ventilator settings currently being used including the mode of mechanical ventilation and a variety of other ventilation-related parameters, for example, peak inspiratory pressure (PIP), positive end-expiratory pressure (PEEP), mean airway pressure ($P_{maw}$), plateau pressure ($P_{plat}$), driving pressure ($P_d$), the area under the inspiratory pressure curve (ipAUC), the area under the expiratory pressure curve (epAUC), static and dynamic respiratory system compliance, airway resistance, estimated work of breathing, peak inspiratory flow (PIF), end-inspiratory flow (EIF), peak expiratory flow (PEF), end-expiratory flow (EEF), inspiratory time (Ti), expiratory time ($T_e$), the ratio of inspiratory to expiratory time (I:E), inspiratory tidal volume (TV), expiratory tidal volume ($TV_e$), and the $TV_e$/$TV_i$ ratio. In addition, to accurately determine the type of ventilator settings, controller 108 must reliably identify the point at which inspiration of the breath transitions to expiration, e.g., $\chi\phi$. Controller 108 identifies $\chi\phi$ by calculating the true transition point from persistent inspiratory (positive) flow to persistent expiratory (negative) flow, while filtering out common signal artifacts that may result in a false positive $\chi\phi$ classification. Accordingly, to identify common ventilation signal artifacts, controller 108 proceeds to step 706.

Figure 8A:
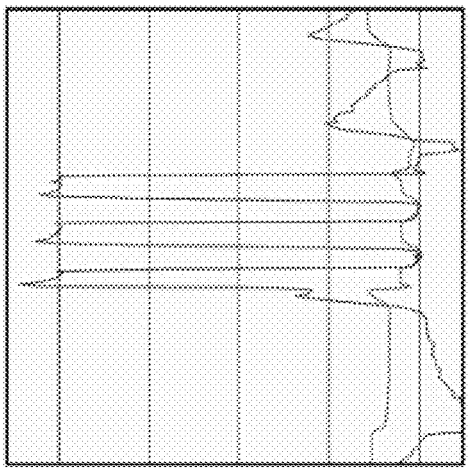
FIGS. 8A-8F illustrate waveforms of various clinical artifacts and patient-ventilator asynchrony subtypes.
Figure 8C:
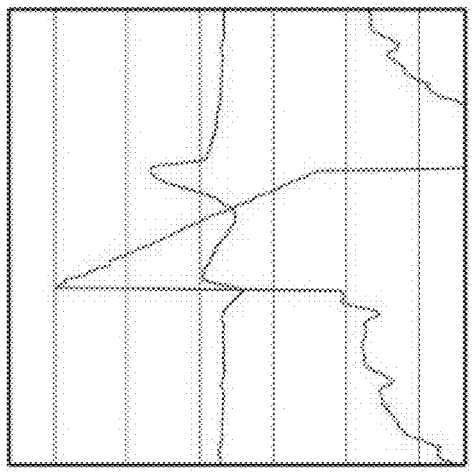
Figure 8B:
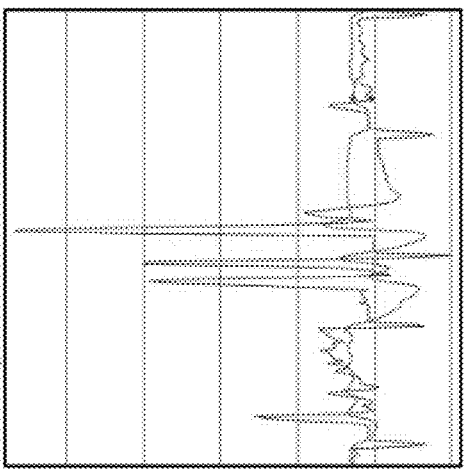

At step 706, controller 108 determines whether one or more artifacts are present in the ventilation based on the measured pressure and flow waveforms from airflow meter 104 and/or one or more sensors 106. An artifact may include, for example, suctioning, cough, and patient-ventilator disconnect. Suctioning refers to closed in-line suctioning of secretions through the endotracheal tube which causes rapid "auto-triggering" of breath delivery that results in the waveform appearance of either multiple successive double trigger or breath stacking asynchronies as shown in FIG. 8A. A cough frequently results in rapid waveform spikes in inspiratory and expiratory flow that can mimic double trigger, breath stacking, flow, and delayed termination asynchrony as shown in FIG. 8B. Cough waveform morphology is highly variable. Preferably, controller 108 may be designed to detect only the subset of cough morphologies that mimic PVA subtypes detectable by controller 108. Patient-ventilator disconnect occurs when the ventilator is not fully connected or disconnected from the patient and may result in the waveform as shown in FIG. 8C. Several ventilator waveform data artifacts commonly observed during routine care shared morphologic similarities to PVAs of interest, resulting in false positive classification of PVA and TVV. Controller 108 may execute a higher-order heuristic algorithm referred to as "artifact correction," that transforms any detected PVA also recognized as a clinical artifact into the class "not PVA." Referring back to FIG. 7, if one or more artifacts are observed at step 706, controller 108 filters out the artifact(s) to avoid false positive detection of a PVA, and returns to step 704 such that device 100 may continue to resuscitate and monitor the patient coupled to device 100. In contrast, if no artifacts are observed at step 704, controller 108 proceeds to step 708.

At step 708, controller 108 determines automatically whether a respiratory failure phenotype, e.g., ARDS, airway obstruction, or pneumothorax, is present based on the measured pressure and flow waveforms data. If a respiratory failure phenotype is detected at step 708, controller 108 proceeds to step 710 and sends information to sensor alarm 112 to communicate an alert to the user. Depending on the type of respiratory failure phenotype detected, controller 108 directs sensor alarm 112 to communicate specific alerts to the user.

Figure 8E:
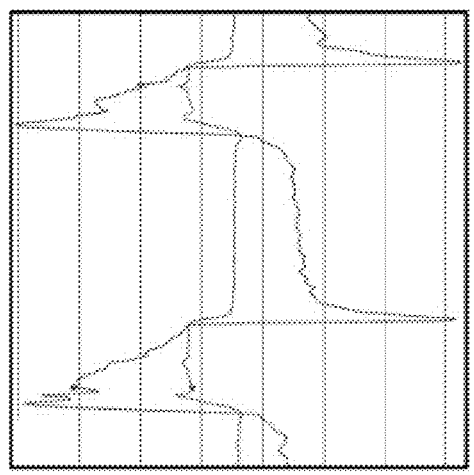

In contrast, if no respiratory failure phenotype is detected by controller 108, controller 108 proceeds to step 712. At step 712, controller 108 classifies the ventilation, as either on-target or off-target. To determine whether the ventilation on-target, e.g., whether the ventilation observed is within normal limits for the patient given the height, weight, gender, and/or age of the patient, or within commonly accepted standards based on the height, weight, gender, and/or age of the patient as inputted in measurement selector 110 at step 702, controller 108 identifies tidal volumes based on the measured pressure and flow waveforms data. For example, controller 108 first identifies $\chi\phi$ as described above while filtering out common sources of signal artifact that are frequent sources of false $\chi\phi$ classification. After identification of $\chi\phi$, controller 108 calculates $TV_i$ by integrating the area under the flow-time curve from the breath start, e.g., positive deflection in flow, until $\chi\phi$ is reached, and $TV_e$ by integrating the area under the flow-time curve from $\chi\phi$ until the breath end. Accurate measurement of $TV_i$ and $TV_e$ is required for the quantitative analysis of off-target TV, and provides essential breath-level metadata used for the algorithmic detection of both PVA and clinical artifacts. After calculation of $TV_i$ and $TV_e$, controller 108 calculates the difference between the measured tidal volumes and the ideal tidal volumes derived from the inputted patient height, weight, gender, and/or age or the ideal tidal volumes based on commonly accepted standards to determine the level of appropriateness. As a result, controller 108 may determine that the observed ventilation is on-target if the level of appropriateness is within normal limits for the patient given the height, weight, gender, and/or age of the patient or within commonly accepted standards based on the height, weight, gender, and/or age of the patient. For example, referring to FIG. 8G, controller 108 calculates $TV_i$ as 365 ml and $TV_e$ as 393 ml, and determines that the observed ventilation, e.g., TVV class, is on-target.

Referring back to FIG. 7, if controller 108 determines that the observed ventilation is on-target at step 712, e.g., synchronous, controller 108 returns to step 704 and device 100 continues to resuscitate and monitor the patient coupled to device 100. If controller 108 determines that the observed ventilation is off-target, e.g., the level of appropriateness is not within normal limits for the patient given the height, weight, gender, and/or age of the patient, controller 108 proceeds to step 714.

At step 714, controller 108 determines the type of off-target ventilation observed. Types of off-target ventilation include, but are not limited to, tidal volume violations, pressure violations, work of breathing violations, and PVA. After determining the type of off-target ventilation, controller 108 proceeds to step 716 and sends information to sensor alarm 112 to communicate an alert to the user. Based on the user-defined settings for clinical decision support alarm thresholds inputted at step 702, the alert may be generated only if the off-target ventilation exceeds the alarm threshold. For example, the alarm threshold may require a 5% or 20% asynchrony, or a 5% or 20% tidal volume violation before controller 108 instructs sensor alarm 112 to communicate an alert to the user. Depending on the type of off-target ventilation observed, device 100 directs sensor alarm 112 to communicate specific alerts to the user and, at step 718, suggests corrective actions for the user to perform the adjustment required to bring the observed ventilation within normal limits for the patient given the height, weight, gender, and/or age of the patient.

For example, if controller determined that the off-target ventilation is a tidal volume violation at step 714, e.g., if a delivered inspiratory volume off-target, controller 108 assesses the ventilation for severity of tidal volume violation logs data information in an event counter. If controller 108 determines that the severity of tidal volume violation exceeded a default or custom event severity or event rate threshold, at step 716 controller 108 generates an alert to the user. Then controller 108 proceeds to step 718 and suggests corrective actions, e.g. to adjust ventilator settings; if still off-target, treat pain/discomfort until symptoms controlled; if still off-target, increase sedation until on-target or deep sedation achieved; if still off-target and ARDS detected or clinically evident, consider paralytic infusion.

In contrast, if controller 108 determines that the off-target ventilation observed is a PVA in step 714, controller 108 identifies the subtype of PVA observed and sends information to sensor alarm 112 to communicate an alert to the user specific to the PVA subtype observed at step 716. For example, PVA subtypes may include, but are not limited to, double trigger asynchrony, breath stacking asynchrony, flow asynchrony, delayed termination asynchrony, premature termination/cycling asynchrony, and auto triggering asynchrony. The ability to sub-classify off-target ventilation may be particularly important for the development of clinical decision support systems where the ability to refine alarm thresholds based on the type, frequency, and severity of off-target ventilation rather than its presence or absence alone may allow better matching of decision support to individual patient and provider needs.

Figure 8D:
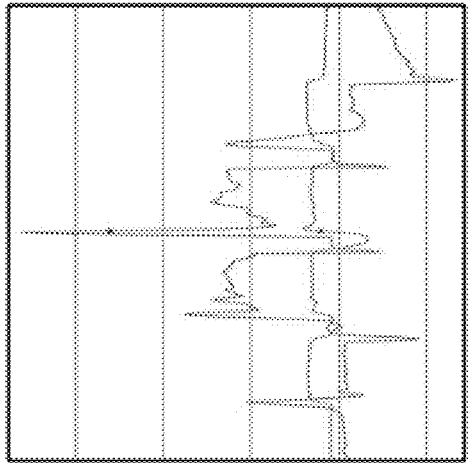
Figure 8F:
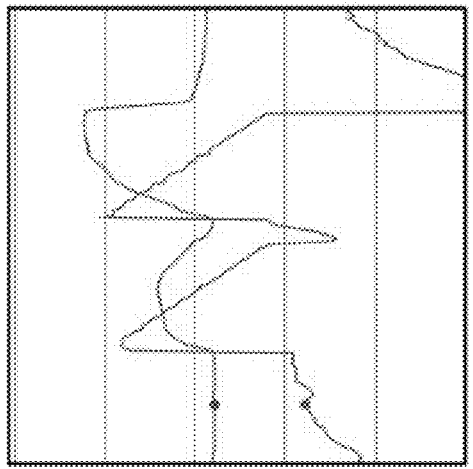
Figure 8G:
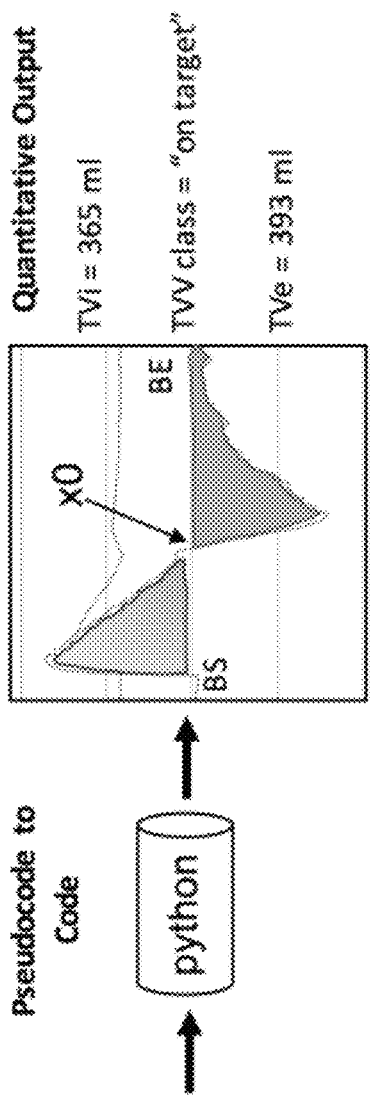
FIG. 8G illustrates an "on-target" observed ventilation as determined in accordance with the principles of the present disclosure.
Figure 8H:
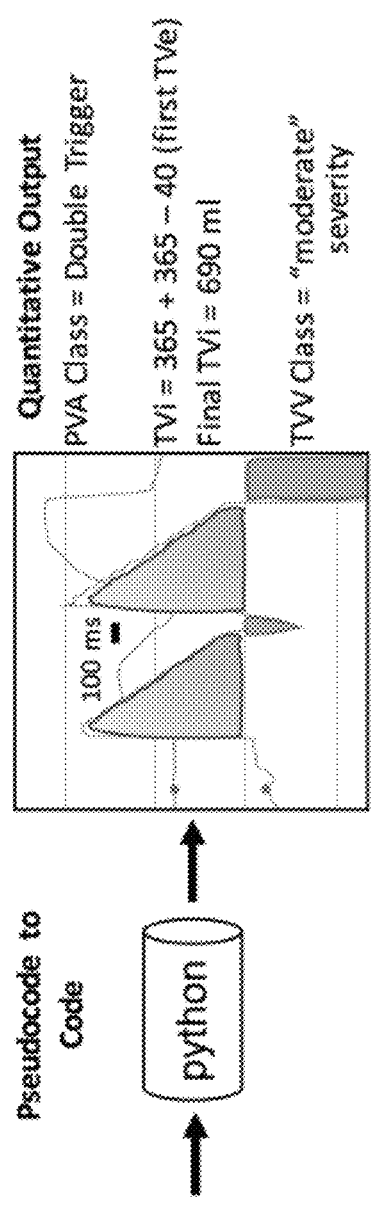
FIG. 8H illustrates a "double trigger asynchrony" patient-ventilator asynchrony as determined in accordance with the principles of the present disclosure.
Figure 9:
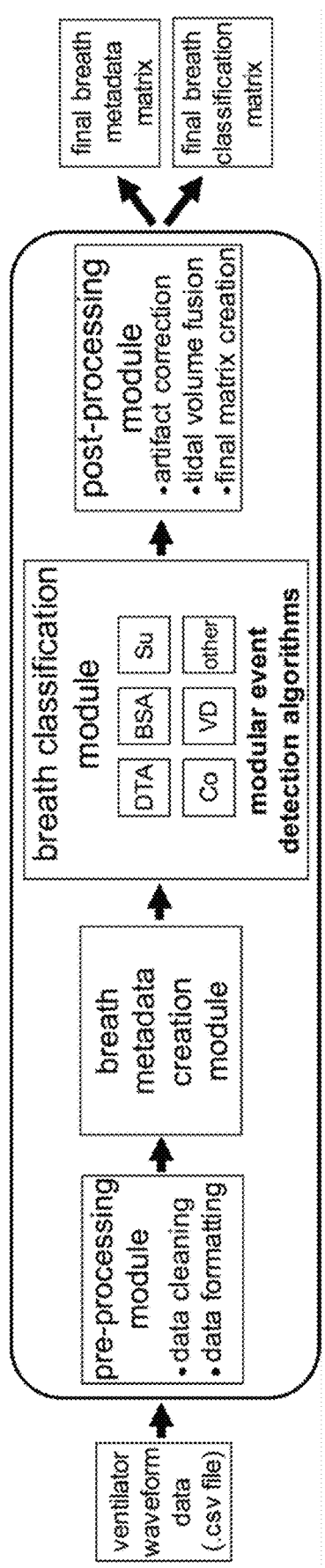
FIG. 9 is a schematic block diagram illustrating an extensible, modular analytic engine, referred to as the ventilator multi-algorithm analytic platform in accordance with the principles of the present disclosure.

Double trigger asynchrony occurs when the ventilator's pre-set inspiratory time is shorter than the patient's desired respiratory time, e.g., the patient continues to inspire after the ventilator has terminated the breath, triggering a second breath immediately after the end of the first without substantive intentional exhalation, and resulting in trapped gas inside the chest. Double trigger asynchrony may result in larger than intended, e.g., double the intended tidal volume, causing potentially harmful distention of lung tissue despite otherwise optimal selection of ventilator settings. Double trigger asynchrony may result in the waveform as shown in FIG. 8D. Referring to FIG. 8H, controller 108 may determine the PVA subtype as double trigger asynchrony when the calculated $TV_e/TV_i$ is less than 25% and the expiratory time is less than or equal to 300 ms. In addition, controller 108 may classify the observed ventilation, e.g., TVV class, as "moderate." Referring back to FIG. 7, if controller 108 determines that the PVA subtype is double trigger asynchrony, controller 108 may, at step 718, suggest corrective actions, e.g., to increase inspiratory time, if in time-cycled mode; decrease flow rate, if in assist control/volume control; increase set tidal volume, if in assist control/volume control and ARDS is not detected or clinically suspected; decrease inspiratory cycle off threshold, if in pressure support or other flow-cycled mode; change mode to pressure targeted mode and either lengthen inspiratory time, if in time-cycled mode, or decrease inspiratory cycle off threshold, if in pressure support/flow-cycled mode; treat pain and/or agitation to decrease respiratory drive and thus patient's desired respiratory rate.

Breath stacking asynchrony occurs when the patient begins to exhale but triggers another breath before complete exhalation has occurred, resulting in trapped gas inside the chest with each stacked breath. Unlike double trigger asynchrony, breath stacking asynchrony results from either a ventilator-set or patient-triggered respiratory rate too fast to allow sufficient time for complete exhalation in between successive breaths. Breath stacking asynchrony is further classified as mild, moderate, or severe based on the amount of gas trapped in the chest with each breath stacking event, and is common in diseases with expiratory flow limitation such as acute exacerbations of asthma or chronic obstructive pulmonary disease ("COPD"). If frequent, breath stacking may result in substantial lung hyperinflation with excessive and potentially damaging distention of lung tissue. In addition to lung injury, frequent breath stacking may result in high levels of intra-thoracic pressure that may decrease blood return from the extra-thoracic organs back to the heart causing low blood pressure that may progress to cardiovascular collapse. These high intra-thoracic pressures may rupture the lung, potentially resulting in low blood oxygen levels and cardiac arrest. Breath stacking asynchrony may result in the waveform as shown in FIG. 8E. Referring back to FIG. 7, if controller 108 determines that the PVA subtype is breath stacking asynchrony, controller 108 may, at step 718, suggest corrective actions, e.g., decrease set respiratory rate; treat pain and/or agitation to decrease respiratory drive and thus patient's desired respiratory rate; decrease inspiratory time, if in time-cycled mode; increase inspiratory cycle off threshold, if in flow-cycled mode; increase dose/frequency of nebulized albuterol bronchodilator therapy and add nebulized ipratropium, if obstruction also present.

Double trigger asynchrony and breath stacking asynchrony both lead to dynamic hyperinflation that can be quantified by calculating the sum of two successive $TV_i$s and subtracting the intervening $TV_e$ to yield a "fused" $TV_i$ that represents the effective distending volume for the lungs. Failure to account for the effective distending volume of a fused breath may lead to failure to detect associations between $TV_i$ and clinical outcomes in research studies, and may lead to volutrauma and worse clinical outcomes if clinically unrecognized and un-remedied. Conversely, excessive detection of false positive OTV may bias research and lead to "alarm fatigue" if implemented in clinical decision support systems. Controller 108 may execute a heuristic event classification algorithm referred to as "TV-fusion" that uses output from TV calculation, DTA classification, and artifact correction algorithms to fuse the component inspiratory and expiratory TVs of DTA breaths and output the effective distending TV of each DTA.

Flow asynchrony occurs in modes of mechanical ventilation that deliver pre-specified, mandatory inspiratory flow when a patient attempts to inhale more rapidly than the rate of pre-specified ventilator-delivered flow, which causes a drop in the pressure in the circuit during inspiration. Flow asynchrony may further be classified as early, late, or pan-inspiratory and may also be classified as mild, moderate, or severe based on the extent to which pressure drops in the ventilator circuit. Flow asynchrony results in increased work of breathing due to inspiratory muscle loading, redirection of blood flow to the muscles of respiration and away from other vital organs that may already be metabolically stressed in the setting of critical illness, and importantly, significant patient distress due to the perception of flow starvation in the setting of respiratory distress. Flow asynchrony may result in the waveform as shown in FIG. 8F. If controller 108 determines that the PVA subtype is flow asynchrony, e.g., decelerating ramp flow delivery pattern, controller 108 may, at step 718, suggest corrective actions, e.g., if early, increase inspiratory flow; if late, decrease set inspiratory flow; increase set tidal volume, if ARDS is not detected and not clinically suspected, or strong risk factor for ARDS is not present, e.g., sepsis, aspiration, blunt trauma, inhalation injury, pancreatitis; treat pain and agitation to decrease respiratory drive/flow hunger; deep sedation, if ARDS with severe hypoxemia is detected or clinically suspected; add paralytic infusion, if deep sedation is inadequate and ARDS with severe hypoxemia is detected or clinically suspected.

Delayed termination asynchrony occurs when the ventilator's set inspiratory time is longer than the patient's desired inspiratory time, e.g., the patient attempts to exhale forcibly prior to complete opening of the ventilator's expiratory valve, resulting in expiratory muscle loading, redirection of blood flow to the muscles of respiration and away from other vital organs that may already be metabolically stressed in the setting of critical illness, and importantly, significant patient distress due to perceived inability to exhale. If controller 108 determines that the PVA subtype is delayed termination asynchrony, controller 108 may, at step 718, suggest corrective actions, e.g., decrease set inspiratory time, if in time-cycled mode; increase inspiratory cycle off threshold, if in flow-cycled mode; increase the set peak flow, if in assist control-volume control; treat pain and agitation to decrease respiratory drive.

If controller 108 determines that the PVA subtype is premature termination/cycling asynchrony, controller 108 may, at step 718, suggest corrective actions, e.g., increase set inspiratory time, if in time-cycled mode; decrease inspiratory cycle off threshold, if in flow-cycled mode. If controller 108 determines that the PVA subtype is auto triggering asynchrony, controller 108 may, at step 718, suggest corrective actions, e.g., increase the set pressure trigger threshold; increase the set flow trigger threshold; check for leak somewhere in the circuit including the endotracheal/tracheostomy tube cuff. If controller 108 determines that the PVA subtype is ineffective trigger/effort, controller 108 may, at step 718, suggest corrective actions, e.g., increase trigger sensitivity, decrease pressure support, increase flow cycling, and/or increase positive end-expiratory pressure ("PEEP").

Upon receiving the corrective action recommendations from device 100, the user may adjust the ventilator, e.g., manual bagging of the patient or the ventilator settings of a mechanical ventilator, to bring the observed ventilation within normal limits for the patient given the size and weight measurements, gender, and/or age of the patient.

Additionally, device 100 may continuously analyze ventilation to determine changes in lung compliance over time and to identify pathological changes over time, e.g., acute respiratory distress syndrome, obstructive lung disease, or pneumothorax. For example, device 100 may continuously analyze $CO_2$ in exhaled breaths to at least identify at least one of inappropriate ventilation rates or pathology, or to predict outcome from cardiac arrest, or may continuously analyze the $O_2$ to identify when the $O_2$ content is either too high or too low for a current physiologic state, and to provide feedback to the user for changes in $O_2$ concentration.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the embodiments disclosed herein may be implemented or performed with a general purpose processor, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

In one or more example embodiments, the functions described may be implemented in hardware, software, or firmware executed on a processor, or any combination thereof. For example, certain embodiments may comprise a computer program product for performing the operations presented herein. Such a computer program product may comprise a computer-readable medium having instructions stored and/or encoded thereon, the instructions being executable by one or more processors to perform the operations described herein. When the functions described herein are implemented in software, the functions may be stored on or transmitted over as one or more instructions or code on a computer-readable medium. Computer readable media includes both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Also, any connection is properly termed a computer-readable medium. For example, if the software is transmitted from a website, server, or other remote source using a coaxial cable, fiber optic cable, twisted pair, digital subscriber line ("DSL"), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc ("CD"), laser disc, optical disc, digital versatile disc ("DVD"), and Blu-ray disc where disks usually reproduce data magnetically, while discs reproduce data optically with lasers. Combinations of the above should also be included within the scope of computer-readable media.

Further, it should be appreciated that modules and/or other appropriate means for performing the methods and techniques described herein may be downloaded and/or otherwise obtained by a device as applicable. For example, such a device may be coupled to a server to facilitate the transfer of means for performing the methods described herein. Alternatively, various methods described herein may be provided via storage means (e.g., RAM, ROM, a physical storage medium such as a CD or flash drive, etc.), such that a device may obtain the various methods upon coupling or providing the storage means to the device. Moreover, any other suitable technique for providing the methods and techniques described herein to a device may be utilized.

Sample Study

A study aimed to develop and validate an integrated MV waveform data acquisition and analysis platform capable of unobtrusive, continuous data collection and breath-by-breath classification of OTV to support clinical outcomes research, translational patient phenotyping, continuous quality improvement, and precision medicine through clinical decision support is described in ADAMS, Jason Y., et al., 'Development and Validation of a Multi-Algorithm Analytic Platform to Detect Off-Target Mechanical Ventilation', Scientific Reports 7, Vol 14980 Nov. 3, 2017 [online], [retrieved 2017-11-08]. Retrieved from the Internet <URL: https://www.nature.com/articles/s41598-017-15052-x#Sec14> <DOI: 10.1038/s41598-017-15052-x>, the entire contents of which is incorporated herein by reference.

As illustrated in FIG. 8, an extensible, modular analytic engine, referred to as the ventilator multi-algorithm analytic platform ("ventMAP"), was developed to automate the quantitative analysis of OTV using rule-based logic derived from clinical bedside interpretation of MV waveforms to determine both $TV_i$ and $TV_e$, two well-recognized forms of PVA associated with hyper-inflation of the lungs, and several common types of VWD "clinical artifacts" that morphologically resemble true PVA. Extensive pre-clinical simulation testing of individual component algorithms was performed with further algorithm derivation and final validation using patient-derived data.

The study focused on the classification of events thought to contribute to VILI through excessive distention of lung tissue including excessive TV, i.e., tidal volume violations ("TVV"), and PVA. Two subtypes of PVA, referred to here as double-trigger asynchrony ("DTA") and breath stacking asynchrony ("BSA"), cause varying degrees of incomplete exhalation in between breaths resulting in a phenomenon referred to as dynamic hyperinflation as described above.

While both DTA and BSA result in dynamic hyperinflation, their distinct pathophysiologic mechanisms merit unique methods of detection. Thus, distinct rule-based classification algorithms were developed and validated to calculate $TV_i$ and $TV_e$, both DTA and BSA, and several common clinical artifacts (suctioning/auto-triggering of the ventilator, a subset of coughs, and transient disconnection from the ventilator) that may result in the false-positive classification of artifacts as PVA. The study aimed for TV accuracy within a pre-specified equivalence threshold of 10% relative to TV measured by the ventilator, and sensitivity and specificity of >90% for each PVA detection algorithm both before and after clinical artifact removal.

The study hypothesized that the ventMAP engine would be able to measure TV with accuracy equivalent to a commercial ventilator, and that the recognition and algorithmic removal of clinical artifacts (referred to here as "artifact correction") would significantly decrease the specificity of PVA detection without compromising sensitivity. The results of the derivation and validation studies are presented as follows.

Accurate measurement of $TV_i$ and $TV_e$ is required for the quantitative analysis of off-target TV, and provides essential breath-level metadata used for the algorithmic detection of both PVA and clinical artifacts. The Puritan Bennett model 840 (PB840) ventilators (Medtronic Corporation) used are accurate to within 10% of the set TV, limited by the inherent imprecision of the ventilator's flow sensor. Thus, a mechanical lung (QuickLung, IngMar Medical) was used to test the accuracy of ventMAP's $TV_i$ and $TV_e$ measurement algorithms. Three separate experiments were performed using three different PB840s, testing ventMAP-derived $TV_i$ and $TV_e$ in a total of 1021 breaths across a range of ventilator modes, trigger mechanisms, set TV, and set inspiratory pressures using a pre-specified equivalence threshold of +/−10%. ventMAP-derived $TV_i$ and $TV_e$ were equivalent to ventilator-derived TV across all measured conditions. The mean ventMAP-derived $TV_i$ and $TV_e$, aggregated across all tested settings of both assist control-volume control ("AC/VC") and assist control-pressure control ("AC/PC") ventilator modes, were equivalent to the TVs recorded by the ventilator's internal software as shown in Table 1 copied below.

TABLE 1

| | $TV_i$ | | $TV_e$ | |
|---|---|---|---|---|
| | % Difference | p-value | % Difference | p-value |
| AC/VC | 3.1% [2.9-3.2] | p < 0.0001 | 5.0% [4.8-5.1] | p < 0.0001 |
| AC/PC | 5.1% [5.0-5.1] | p < 0.0001 | 5.0% [4.9-5.1] | p < 0.0001 |

Table 1 illustrates the difference between ventMAP-calculated and ventilator-recorded tidal volumes in volume control and pressure control modes. Differences reported as mean difference, 95% confidence interval, and p-value for equivalence test with pre-specified equivalence margin of +/−10% ($H_0$: Ventilator and ventMAP are not equivalent). Positive values indicate that ventilator volumes were larger than ventMAP volumes.

In the study, algorithm performance was assessed for sensitivity, specificity, and overall accuracy using logistic regression to control for potential similarities in waveform characteristics within patients, and differential event rates between patients. Algorithm performance was compared to a gold standard classification data set derived from multi-clinician manual annotation of the same breaths, e.g., data including nearly 10,000 breaths from 33 patients including multiple ventilator modes and acute indications for MV. For example, as shown in Table 2 copied below, in the derivation cohort, ventMAP achieved a sensitivity, specificity, and overall accuracy of 0.988, 0.965, and 0.967, respectively, for the classification of DTA. ventMAP performance was then tested without further modification in a separate validation data set consisting of 4644 manually annotated breaths from 17 mechanically ventilated patients. In the validation cohort, ventMAP's performance decreased somewhat with sensitivity, specificity, and overall accuracy of 0.940, 0.920, and 0.922, respectively, but remained above the pre-specified goal of ≥90% for all three measures. In addition, in the derivation cohort, ventMAP achieved a sensitivity, specificity, and overall accuracy of 0.985, 0.984, and 0.984, respectively, for the classification of BSA, and in the validation cohort, performance declined slightly with sensitivity, specificity, and overall accuracy of 0.967, 0.980, and 0.977, respectively.

TABLE 2

| Event Type | Derivation Data Set (n = 16) | | | Validation Data Set (n = 17) | | |
| --- | --- | --- | --- | --- | --- | --- |
| | Accuracy | Sensitivity | Specificity | Accuracy | Sensitivity | Specificity |
| Double Trigger | 0.967 [0.962, 0.971] | 0.988 [0.972, 0.996] | 0.965 [0.960, 0.970] | 0.922 [0.914, 0.930] | 0.94 [0.913, 0.960] | 0.92 [0.912, 0.928] |
| Breath Stacking | 0.984 [0.980, 0.987] | 0.985 [0.975, 0.992] | 0.984 [0.980, 0.987] | 0.977 [0.973, 0.981] | 0.967 [0.955, 0.977] | 0.98 [0.975, 0.985] |
| Cough, Suction, Vent Disconnect Combined | 0.992 [0.989, 0.994] | 0.907 [0.859, 0.943] | 0.995 [0.993, 0.997] | 0.981 [0.977, 0.985] | 0.879 [0.841, 0.912] | 0.989 [0.986, 0.992] |

After optimization of artifact correction algorithms in the derivation cohort, ventMAP was tested with and without the use of artifact correction in the validation cohort to test the hypothesis that artifact correction would improve the specificity of PVA detection without reducing sensitivity. As shown in Table 3 copied below, in the derivation cohort, use of artifact correction resulted in a 2.8% [95% confidence intervals ("CI") 0.9-4.7%; p=0.006] improvement in DTA classification specificity and a non-significant 0.6% [95% CI −2.0-0.8%; p=0.361] decrease in sensitivity, whereas artifact correction had no significant effect on BSA classification. In the validation cohort, the study observed a 7.1% [1.1-13.2%; p=0.024] improvement in the specificity of DTA classification and a non-significant 3.0% [−6.3-0.3%; p=0.067] decrease in sensitivity. Artifact correction resulted in a 0.6% [0.2-1.0%; p=0.009] improvement in the specificity of BSA classification, and a non-significant 0.3% [−0.9-0.2%; p=0.189] decrease in sensitivity.

TABLE 3

| | Derivation Data Set (n = 16) | | | Validation Data Set (n = 17) | | |
| --- | --- | --- | --- | --- | --- | --- |
| | Accuracy | Sensitivity | Specificity | Accuracy | Sensitivity | Specificity |
| Double Trigger | 2.60% [0.8, 4.3] p = 0.007 | −0.60% [−2.0, 0.8] p = 0.361 | 2.80% [0.9, 4.7] p = 0.006 | 6.20% [1.0, 11.4] p = 0.021 | −3.00% [−6.3, 0.3] p = 0.067 | 7.10% [1.1, 13.2] p = 0.024 |
| Breath Stacking | 0.40% [−0.1, 0.8] p = 0.105 | −0.90% [−1.7, 0.16] p = 0.021 | 0.60% [0, 12.7] p = 0.047 | 0.40% [0.03, 0.7] p = 0.036 | −0.30% [−0.9, 0.2] p = 0.189 | 0.60% [0.2, 1.0] p = 0.009 |

Figures 10A, 10B:
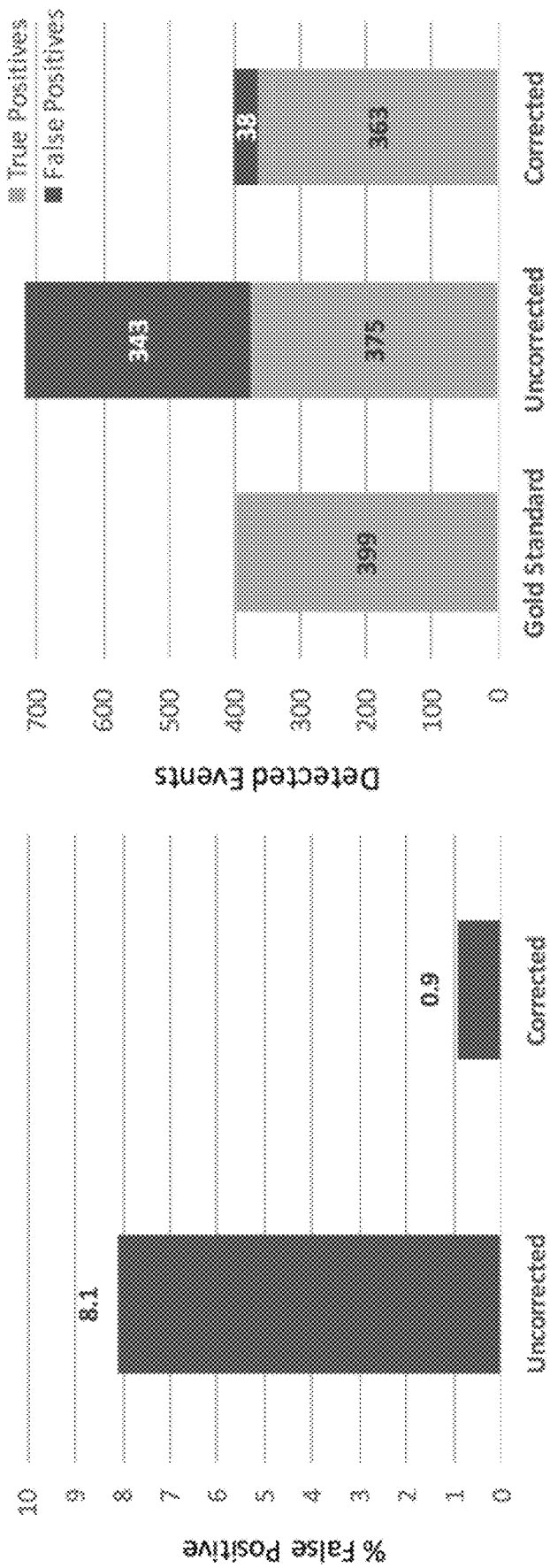
FIGS. 10A and 10B illustrate the detection rate of DTA with and without artifact correction in accordance with the principles of the present disclosure.

As shown in FIGS. 10A and 10B, the study observed a 9-fold reduction in the false-positive detection rate of DTA with the use of artifact correction resulting in a 44.2% decrease in the total number of detected DTA events from 718 without artifact correction to 401 breaths with use of artifact correction, with 399 true DTA events in the gold standard data set.

The study calculated the mean $TV_i$ and the distribution of TVV (on-target versus off-target, and the relative severity of off-target breaths) across all DTA breaths in the validation cohort, with and without the use of the TV-fusion algorithm. In the validation data set, mean $TV_i$ for DTAs was significantly higher when TV-fusion was employed, with a mean $TV_i$ of 293.3 ml (95% CI, 278.6-308.0) without TV-fusion and 562.2 ml (95% CI, 529.7-594.7; p<0.0001 for the difference between means) with T-V fusion. Clinically, prescribed TV are based on predicted body weight ("PBW") derived from sex and height, with $TV_i$ of ≤6.5 ml/kg of PBW representing the standard of care for patients with severe hypoxemic respiratory failure. In the study, the average height of a U.S. female was used to normalize all DTA TVs in the validation cohort before and after TV-fusion. After identifying all potential DTA breaths and removing false positives through artifact correction, off-target breaths was stratified with and without TV-fusion as mild, moderate, or severe based on the extent to which a given breath exceeded a target of ≤6.5 ml/kg as shown in FIG. 11A. As shown in FIG. 11B, TVV was significantly more severe amongst fused than unfused breaths, with a mean increase in TVV class of 1.58 [95% CI: 1.02-2.15, p<0.0001] per breath.

Although the foregoing has included detailed descriptions of some embodiments by way of illustration and example, it will be readily apparent to those of ordinary skill in the art in light of the teachings of these embodiments that numerous changes and modifications may be made without departing from the spirit or scope of the appended claims.

What is claimed is:

1. A resuscitation and ventilation monitoring system, the system comprising:
    a processor; and
    a non-transitory computer-readable medium having instructions that, when executed by the processor, cause the processor to:
        receive user input from a user, the user input comprising at least one of a height, weight, gender, or age of a patient;
        during a ventilation of the patient, generate a ventilation signal indicative of a current mode of ventilation and associated ventilator settings based on at least one of airflow, pressure, oxygen, or carbon dioxide measurements received from at least one of an airflow meter or one or more sensors in fluid communication with airflows exchanged with lungs of the patient;
        identify and filter out at least one clinical artifact present in the ventilation signal, wherein each of the at least one clinical artifact corresponds to a ventilation event other than patient ventilator asynchrony;
        determine that the ventilation corresponds to patient ventilator asynchrony in response to determining that the current mode of ventilation and associated ventilator settings are not within a predetermined limit defined by the user input; and based on the determination that the ventilation corresponds to patient ventilator asynchrony:

identify a subtype of patient ventilator asynchrony observed, wherein the patient ventilator asynchrony subtype is at least one of a double trigger asynchrony, breath stacking asynchrony, flow asynchrony, delayed termination asynchrony, early termination asynchrony, forced exhalation asynchrony, and ineffective trigger asynchrony;

generate an alert indicating the presence of patient ventilator asynchrony; and suggest user-implementable corrective action, via a user interface, to adjust ventilator settings of a mechanical ventilator in order to correct the patient ventilator asynchrony.

2. The resuscitation and ventilation monitoring system of claim 1, further comprising a measurement selector configured to receive the user input from the user, wherein the measurement selector includes a surrogate marker including at least one of numbers, letters, or colors.

3. The resuscitation and ventilation monitoring system of claim 2, wherein the surrogate marker includes a plurality of colored options, each of the plurality of colored options corresponding to colors and associated measurement increments defined by a Broselow Tape; and wherein each of the colors and associated measurement increments defined by the Broselow Tape corresponds to a respective predetermined limit of the ventilation.

4. The resuscitation and ventilation monitoring system of claim 1, wherein the user input further comprises user-defined settings for clinical decision support alarm thresholds, and wherein the alert is generated in response to the patient ventilator asynchrony exceeding the clinical decision support alarm thresholds.

5. The resuscitation and ventilation monitoring system of claim 1, wherein the processor receives the at least one of airflow, pressure, oxygen, or carbon dioxide measurements from at least one of the airflow meter or one or more sensors via at least one of WiFi, Bluetooth, serial communication, or cellular communication.

6. The resuscitation and ventilation monitoring system of claim 5, wherein the processor sends raw ventilation data and derived information including clinical decision support via at least one of WiFi, Bluetooth, serial communication, or cellular communication, to one or more external destinations comprising electronic medical record systems or telemedicine systems.

7. The resuscitation and ventilation monitoring system of claim 1, wherein the at least one clinical artifact corresponds to at least one of a suction event, a cough, or a patient-ventilator disconnect.

8. The resuscitation and ventilation monitoring system of claim 1, wherein the instructions of the non-transitory computer-readable medium, when executed by the processor, further cause the processor to determine whether a respiratory failure phenotype is present in the ventilation, the respiratory failure phenotype being at least one of acute respiratory distress syndrome, obstructive lung disease, or pneumothorax.

9. The resuscitation and ventilation monitoring system of claim 1, wherein the predetermined limit of the ventilation defined by the user input comprises a corresponding range of acceptable respiratory rates and tidal volumes.

10. The resuscitation and ventilation monitoring system of claim 1, wherein the predetermined limit of the ventilation comprises commonly accepted standards of practice based on the user input.

11. The resuscitation and ventilation monitoring system of claim 1, wherein the alert generated is a visual alert.

12. The resuscitation and ventilation monitoring system of claim 1, wherein the alert generated is an audio alert.

13. The resuscitation and ventilation monitoring system of claim 1, wherein the suggested corrective action is based on the patient ventilator asynchrony subtype.

14. The resuscitation and ventilation monitoring system of claim 1, wherein the instructions of the non-transitory computer-readable medium, when executed by the processor, further cause the processor to determine whether a delivered inspiratory volume is on-target or off-target.

15. The resuscitation and ventilation monitoring system of claim 1, wherein the instructions of the non-transitory computer-readable medium, when executed by the processor, further cause the processor to continuously analyze ventilation to determine changes in lung compliance over time and to identify a pathology that includes at least one of acute respiratory distress syndrome, obstructive lung disease, or pneumothorax.

16. The resuscitation and ventilation monitoring system of claim 1, wherein at least one of the one or more sensors comprises a $CO_2$ sensor in fluid communication with airflows exchanged with lungs of the patient.

17. The resuscitation and ventilation monitoring system of claim 1, wherein the instructions of the non-transitory computer-readable medium, when executed by the processor, further cause the processor to continuously analyze $CO_2$ in exhaled breaths to at least identify at least one of inappropriate ventilation rates or pathology, or to predict outcome from cardiac arrest.

18. The resuscitation and ventilation monitoring system of claim 1, wherein at least one of the one or more sensors comprises an $O_2$ sensor in fluid communication with airflows exchanged with lungs of the patient.

19. The resuscitation and ventilation monitoring system of claim 1, wherein the instructions of the non-transitory computer-readable medium, when executed by the processor, further cause the processor to:

continuously analyze measurements of $O_2$ concentration in the airflows;

identify when the $O_2$ concentration is either too high or too low for a current physiologic state; and provide feedback to the user for changes in the $O_2$ concentration.

20. The resuscitation and ventilation monitoring system of claim 1, wherein the instructions of the non-transitory computer-readable medium, when executed by the processor, further cause the processor to continuously analyze clinical data obtained via at least one of WiFi, Bluetooth, serial communication, or cellular communication from one or more external sources comprising electronic medical records, and from one or more physiologic patient monitoring devices comprising pulse oximeters, non-invasive blood pressure cuffs, invasive arterial blood pressure monitors, intracranial monitors, or cardiac and circulatory physiology monitors.

21. The resuscitation and ventilation monitoring system of claim 1, wherein the instructions of the non-transitory computer-readable medium, when executed by the processor, further cause the processor to transmit raw ventilation data or higher order information derived from the resuscitation and ventilation monitoring system via at least one of WiFi, Bluetooth, serial communication, or cellular communication, to one or more external destinations comprising electronic medical record systems or telemedicine systems.

22. The resuscitation and ventilation monitoring system of claim 1, wherein at least one of the one or more sensors comprises a pressure sensor in fluid communication with airflows exchanged with lungs of the patient.

23. A non-transitory computer-readable medium having instructions that, when executed by a processor of a ventilator, cause the processor to:
receive user input from a user, the user input comprising at least one of a height, weight, gender, or age of a patient;
during a ventilation of the patient, generate a ventilation signal indicative of a current mode of ventilation and associated ventilator settings based on airflow measurements received from at least one of an airflow meter or one or more sensors in fluid communication with airflows exchanged with lungs of the patient;
identify and filter out at least one clinical artifact present in the ventilation signal, wherein each of the at least one clinical artifact corresponds to a ventilation event other than patient ventilator asynchrony;
determine that the ventilation corresponds to patient ventilator asynchrony in response to determining that the current mode of ventilation and associated ventilator settings are not within a predetermined limit defined by the user input; and
based on the determination that the ventilation corresponds to patient ventilator asynchrony:
identify a subtype of patient ventilator asynchrony observed, wherein the patient ventilator asynchrony subtype is at least one of a double trigger asynchrony, breath stacking asynchrony, flow asynchrony, delayed termination asynchrony, early termination asynchrony, forced exhalation asynchrony, and ineffective trigger asynchrony;
generate an alert indicating the presence of patient ventilator asynchrony; and
suggest user-implementable corrective action, via a user interface, to adjust ventilator settings of a mechanical ventilator in order to correct the patient ventilator asynchrony.

24. The non-transitory computer-readable medium of claim 23,
wherein the suggested corrective action is based on the patient ventilator asynchrony subtype.

25. The non-transitory computer-readable medium of claim 23, wherein the instructions, when executed by the processor, further cause the processor to determine whether a respiratory failure phenotype is present in the ventilation.

26. The non-transitory computer-readable medium of claim 23, wherein the instructions, when executed by the processor, further cause the processor to continuously analyze ventilation to determine changes in lung compliance over time and to determine a presence of at least one of acute respiratory distress syndrome, obstructive lung disease, or pneumothorax.

27. A method of monitoring resuscitation and ventilation of a patient, the method comprising:
receiving user input from a user via a measurement selector, the user input comprising at least one of a height, weight, gender, or age;
during a ventilation of the patient, generating a ventilation signal indicative of a current mode of ventilation and associated ventilator settings based on airflow measurements received from at least one of an airflow meter or one or more sensors in fluid communication with airflows exchanged with lungs of the patient;
identifying and filtering out at least one clinical artifact present in the ventilation signal, wherein each of the at least one clinical artifact corresponds to a ventilation event other than patient ventilator asynchrony;
determining that the ventilation corresponds to patient ventilator asynchrony in response to determining that the current mode of ventilation and associated ventilator settings are not within a predetermined limit defined by the user input; and
based on the determining that the ventilation corresponds to patient ventilator asynchrony:
identifying a subtype of patient ventilator asynchrony observed, wherein the patient ventilator asynchrony subtype is at least one of a double trigger asynchrony, breath stacking asynchrony, flow asynchrony, delayed termination asynchrony, early termination asynchrony, forced exhalation asynchrony, and ineffective trigger asynchrony;
generating an alert indicating the presence of patient ventilator asynchrony; and
suggesting user-implementable corrective action, via a user interface, to adjust ventilator settings of a mechanical ventilator in order to correct the patient ventilator asynchrony.

28. The method of claim 27,
wherein the suggested corrective action is based on the patient ventilator asynchrony subtype.

29. The method of claim 27, further comprising determining whether a respiratory failure phenotype is present in the ventilation.

30. The method of claim 27, further comprising continuously analyzing ventilation to determine changes in lung compliance over time and to identify pathological changes over time, the pathological changes including acute respiratory distress syndrome, obstructive lung disease, or pneumothorax.

31. The method of claim 27, further comprising:
continuously analyzing ventilation data in concert with clinical data derived from external sources to detect that a current method of ventilation delivery may contribute to development of or worsening of circulatory shock, contribute to development of or worsening of end-organ dysfunction, or is inadequate to meet physiologic needs of a given acute illness; and
prompting the user to consider adjustment of ventilation settings.

32. The method of claim 27, wherein the alert is specific to the subtype of patient ventilator asynchrony observed.

33. The resuscitation and ventilation monitoring system of claim 1, wherein the one or more sensors in fluid communication with airflows exchanged with lungs of the patient includes an $O_2$ sensor configured to measure $O_2$ concentration, and wherein the instructions, when executed by the processor, further cause the processor to:
- analyze measurements of $O_2$ concentration received from the $O_2$ sensor,
- analyze clinical data obtained from one or more pulse oximeters,
- continuously analyze pressure and flow waveforms, and
- determine whether acute respiratory distress syndrome is present in the patient.

34. The non-transitory computer-readable medium of claim 23, wherein the one or more sensors in fluid communication with airflows exchanged with lungs of the patient includes an $O_2$ sensor configured to measure $O_2$ concentration, and
wherein the instructions, when executed by the processor, further cause the processor to:
- analyze measurements of $O_2$ concentration received from the $O_2$ sensor,
- analyze clinical data obtained from one or more pulse oximeters,
- continuously analyze pressure and flow waveforms, and
- determine whether acute respiratory distress syndrome is present in the patient.

35. The method of claim 27, wherein the one or more sensors in fluid communication with airflows exchanged with lungs of the patient includes an $O_2$ sensor configured to measure concentration, and
wherein the method further comprises:
- analyzing measurements of $O_2$ concentration received from the $O_2$ sensor,
- analyzing clinical data obtained from one or more pulse oximeters,
- continuously analyzing pressure and flow waveforms, and
- determining whether acute respiratory distress syndrome is present in the patient.

\* \* \* \* \*